US008871489B2

(12) United States Patent
Grabar et al.

(10) Patent No.: US 8,871,489 B2
(45) Date of Patent: Oct. 28, 2014

(54) **METABOLIC EVOLUTION OF *ESCHERICHIA COLI* STRAINS THAT PRODUCE ORGANIC ACIDS**

(75) Inventors: Tammy Grabar, Reading, MA (US); Wei Gong, Woburn, MA (US); R. Rogers Yocum, Lexington, MA (US)

(73) Assignee: Myriant Corporation, Quincy, MA (US)

( * ) Notice: Subject to any disclaimer, the term of this patent is extended or adjusted under 35 U.S.C. 154(b) by 0 days.

(21) Appl. No.: 13/394,176

(22) PCT Filed: Nov. 17, 2010

(86) PCT No.: PCT/US2010/057111
§ 371 (c)(1),
(2), (4) Date: Mar. 5, 2012

(87) PCT Pub. No.: WO2011/123154
PCT Pub. Date: Oct. 6, 2011

(65) Prior Publication Data
US 2012/0202259 A1    Aug. 9, 2012

Related U.S. Application Data

(60) Provisional application No. 61/281,483, filed on Nov. 18, 2009.

(51) Int. Cl.
| | |
|---|---|
| *C12N 1/20* | (2006.01) |
| *C12N 1/00* | (2006.01) |
| *C12N 15/74* | (2006.01) |
| *C07H 21/04* | (2006.01) |
| *C07K 14/245* | (2006.01) |
| *C12P 7/46* | (2006.01) |
| *C12P 7/54* | (2006.01) |
| *C12P 7/40* | (2006.01) |

(52) U.S. Cl.
CPC ............. *C07K 14/245* (2013.01); *C12P 7/46* (2013.01); *C12P 7/54* (2013.01); *C12P 7/40* (2013.01)
USPC ... 435/252.3; 435/145; 435/243; 435/252.31; 435/252.32; 435/252.33; 435/252.34; 435/252.35; 435/471; 536/23.2

(58) Field of Classification Search
None
See application file for complete search history.

(56) References Cited

U.S. PATENT DOCUMENTS

| | | | |
|---|---|---|---|
| 5,168,056 | A | 12/1992 | Frost |
| 5,169,768 | A | 12/1992 | Backman |
| 5,602,030 | A | 2/1997 | Ingram et al. |
| 6,962,794 | B2 | 11/2005 | Valle et al. |
| 7,223,567 | B2 | 5/2007 | Ka-Yiu et al. |
| 7,371,558 | B2 | 5/2008 | Cervin et al. |
| 7,524,660 | B2 | 4/2009 | Caimi et al. |
| 7,629,162 | B2 | 12/2009 | Zhou et al. |
| 2004/0214294 | A1 | 10/2004 | Rieping |
| 2007/0037265 | A1 | 2/2007 | Zhou et al. |
| 2008/0176302 | A1 | 7/2008 | Cervin et al. |
| 2009/0148914 | A1 | 6/2009 | Causey et al. |

FOREIGN PATENT DOCUMENTS

| | | |
|---|---|---|
| WO | 2008115958 A2 | 9/2008 |
| WO | 2010115067 A2 | 10/2010 |

OTHER PUBLICATIONS

Zhang et al. Proc Natl Acad Sci U S A, Dec. 1, 2009; 106(48):20180-5, Epub Nov. 16, 2009.*
Sasaki, M. et al. "Simultaneous utilization of D-cellobiose, D-glucose, and D-xylose by recombinant *Corynebacterium glutamicum* under oxygen-deprived conditions" Applied Microbiology and Biotechnology, 2008, pp. 691-699, vol. 81.
Sedlak, M. et al. "Characterization of the effectiveness of hexose transporters for transporting xylose during glucose and xylose co-fermentation by a recombinant *Saccharomyces* yeast" Yeast, 2004, pp. 671-684, vol. 21.
Soberon, X. et al. "Engineering transport protein function: theoretical and technical consideratios using the sugar-transporting phosphotransferase system of *Escherichia coli* as a model system" Journal of Molecular and Microbiological Biotechnology, 2006, pp. 302-307, vol. 11.
Trinh, C. T. et al. (2008) "Minimal *Escherichia coli* cell for the most efficient production of ethanol from hexoses and pentoses" Applied and Environmental Microbiology, 2008, pp. 3634-3643, vol. 74.
Venter, H. et al. "Molecular dissection of membrane-transport proteins: mass spectrometry and sequence determination of the galactose-H+ symport protein, GalP of *Escherichai coli* and quantitative assay of the incorporation of [ring-2-13C]histidine and 15NH3" Biochemical Journal, 2002, pp. 243-252, vol. 363.
Wahlbom, C. F. et al. "Molecular analysis of a *Saccharomyces cerevisae* mutant with improved ability to utilize xylose shows enhanced expression of proteins involved in transport, initial xylose metabolism, and the pentose phosphate pathway" Applied and Environmental Microbiology, 2003, pp. 740-746, vol. 69.
Wang, Q. et al. "Expression of galactose permease and pyruvate carboxylase in *Escherichia coli* ptsG mutant increases the growth rate and succinate yiled under anaerobic conditions" Biotechnology Letters, 2006, pp. 89-93, vol. 28.
Yi, J. et al. "Altered glucose transport and shikimate pathway product yields in E. coli" Biotechnology Progress, 2003, pp. 1450-1459, vol. 19.

(Continued)

*Primary Examiner* — Iqbal H Chowdhury
(74) *Attorney, Agent, or Firm* — Ramasamy Mannan

(57) ABSTRACT

This invention relates to the metabolic evolution of a microbial organism previously optimized for producing an organic acid in commercially significant quantities under fermentative conditions using a hexose sugar as sole source of carbon in a minimal mineral medium. As a result of this metabolic evolution, the microbial organism acquires the ability to use pentose sugars derived from cellulosic materials for its growth while retaining the original growth kinetics, the rate of organic acid production and the ability to use hexose sugars as a source of carbon. This invention also discloses the genetic change in the microorganism that confers the ability to use both the hexose and pentose sugars simultaneously in the production of commercially significant quantities of organic acids.

13 Claims, 11 Drawing Sheets

(56) References Cited

OTHER PUBLICATIONS

Zhang, X. et al. "Metabolic evolution of energy-conserving pathways for succinate production in *Escherichia coli*" Proceeding of National Academy of Sciences USA, 2009, pp. 20180-20185, vol. 106.

Grossiord, B. P. et al. "Characterization, expression, and mutation of the *Lactococcus lactis* galPMKTE genes, involved in galactose utilization via the Leloir Pathway" Journal of Bacteriology, 2003, pp. 870-878, vol. 185.

Paulsen, I. T. et al. "Characterization of glucose-specific catabolite repression-resistant mutants of *Bacillus subtilis*: Identification of a novel hexose:H+ symporter" Journal of Bacteriology, 1998, pp. 498-504, vol. 180.

Bertilsson, M. et al. "Prefermentation improves xylose utilization in simultaneous saccharification and co-fermentation of pretreated spruce" Biotechnology for Biofuels, 2009, pp. 2: 8 (Biomed Central. Published Apr. 8, 2009) doi:10.1186/1754-6834-2-8.

Biville, F. et al. "Mutants of *Escherichia coli* producing pyrroloquinoline quinine" Journal of General Microbiology, 1991, pp. 1775-1782, vol. 137.

Cairns, M. T. et al. "Cytochalasin B as a probe of protein structure and substrate recognition by the Galactose/H+ transporter of *Escherichia coli*" Journal of Biological Chemistry, 1991, pp. 8176-8183, vol. 266.

Chen, R. et al. "Comparative studies of *Escherichia coli* strains using different glucose uptake systems: Metabolism and energetic" Biotechnology and Bioengineering, 1997, pp. 583-590, vol. 56.

Chen, T. et al. "An in vivo, label-free quick assay for xylose transport in *Escherichia coli*." Analytical Biochemistry, 2009, pp. 63-67, vol. 390.

Chin, J. W. et al. "Analysis of NADPH supply during xylitol production by engineered *Escherichia coli*" Biotechnology and Bioengineering, 2009, pp. 209-220, vol. 102.

Cirino, J. et al. "Engineering *Escherichia coli* for xylitol production from glucose-xylose mixtures" Biotechnology and Bioengineering, 2006, pp. 1167-1176,vol. 95.

Castro, R. et al. "Characterization of the individual glucose uptake systems of *Lactococcus lactis*: mannose-PTS, cellobiose-Pts and the novel GlcU permease" Molecular Microbiology, 2009 pp. 795-806, vol. 71.

Causey, T. B. et al. "Engineering *Escherichia coli* for efficient conversion of glucose to pyruvate" Proceedings of National Academy of Sciences USA, 2004, pp. 2235-2240, vol. 101.

De Anda, R. et al. "Replacement of the glucose phosphotransferase transport system by galactose permease reduces acetate accumulation and improves process performance of *Escherichia coli* for recombinant protein production without impairment of growth rate" Metabolic Engineering, 2006, pp. 281-290, vol. 8.

Deutscher, J. et al. "How phosphotransferase system-related protein phsophorylation regulates carbohydrate metabolism in bacteria" Microbiology and Molecular Biology Reviews, 2006, pp. 939-1031, vol. 70.

Deutscher, J. "The mechanism of carbon catabolite repression in bacteria" Current Opinion in Microbiology, 2008, pp. 87-93, vol. 11.

Dien, B.S. et al. "Fermentation of sugar mixtures using *Escherichia coli* catabolite repression mutants engineered for production of L-lactic acid" Journal of Industrial Microbiology & Biotechnology, 2002, pp. 221-227, vol. 29.

Flores, N. et al. "Growth recovery on glucose under aerobic condition of an *Escherichia coli* strain carrying a phosphoenolpyruvate:carbohydrate phosphotransferase system deletion by inactivating arcA and overexpressing the genes coding for glucokinase and galactose permease" Journal of Molecular Microbiology and Biotechnology, 2007, pp. 105-116, vol. 13.

Gorke, B. et al. "Carbon catabolite repression in bacteria; many ways to make the most out of nutrients" Nature Review Microbiology 2008, pp. 613-624, vol. 6.

Henderson, P. J. F. et al. "Transport of galactose, glucose and their molecular analogues by *Escherichia coli* K12" Biochemical Journal. 1977, pp. 309-320, vol. 162.

Henderson, P. J. "Proton-linked sugar transport systems in bacteria" Journal of Bioenergetics and Biomembrane, 1990, pp. 525-569, vol. 22.

Hernandez-Montalvo, V. et al. "Characterization of sugar mixtures utilization by an *Escherichia coli* mutant devoid of the phosphotransferase system" Applied Microbiology and Biotechnology, 2001, pp. 186-191, vol. 57.

Ho, N. W. Y. et al. "Genetically engineered *Sacchromyces* yeast capable of effective cofermentation of glucose and xylose" Applied and Environmental Microbiology, 1998, pp. 1852-1859, vol. 64.

Jantama, K. et al. "Combining metabolic engineering and metabolic evolutions to develop non-recombinant strains of *Escherichia coli* C that produce succinate and malate" Biotechnology and Bioengineering, 2008a, pp. 1140-1153, vol. 99.

Jantama, K. et al."Eliminating side products and increasing succinate yields in engineered strains of *Escherichia coli* C" Biotechnology and Bioengineering, 2008b, pp. 881-893, vol. 101.

Kasahara, T. et al. (2003) "Transmembrane segments 1, 5, 7, and 8 are required for high-affinity glucose transport by *Saccharomyces cerevisiae* Hxt2 tranporter." Biochemical Journal, 2003, pp. 247-252, vol. 372.

Kasahara, T. et al. "Comprehensive chimeric analysis of amino acid residues critical for high affinity glucose transport by Hxt2 of *Saccharomyces cerevisiae*" Journal of Biological Chemistry, 2004, pp. 30274-30278, vol. 279.

Kasahara, T. et al. "Identification by comprehensive chimeric analysis of a key residue responsible for high affinity glucose transport by yeast HXT2" Journal of Biological Chemistry, 2007, pp. 13146-13150, vol. 282.

Kasahara, T. et al. "Eight amino acid residues in transmembrane segments of yeast glucose transporter HXt2 are required for high affinity transport." Journal of Biological Chemistry, 2006, pp. 18532-18538, vol. 281.

Khankal, R. et al. "Role of xylose transporters in xylitol production from engineered *Escherichia coli*." Journal of Biotechnology, 2008, pp. 246-252, vol. 134.

Kilian, S. G. et al. "Transport of xylose and glucose in the xylose fermenting yeast *Pichia stipitis*" Applied Microbiology and Biotechnology, 1988, pp. 545-548, vol. 27.

Kim, Y. et al. "Construction of an *Escherichia coli* K-12 mutant for homoethnologenic fermentation of glucose or xylose without foreign genes" Applied and Environmental Microbiology, 2007, pp. 1766-1771, vol. 73.

Kuyper, M. et al. "Evolutionary engineering of mixed-sugar utilization by a xylose-fermenting *Saccharomyces cerevisiae* strain" FEMS Yeast Research, 2005, pp. 925-934, vol. 5.

Law, C. J. et al. "Ins and outs of major facilitator superfamily antiporters" Annual Review of Microbiology, 2008, pp. 289-305, vol. 62.

Leandro, M. J. et al. "Two glucose/xylose transporter genes from the yeast *Candida intermedia*: first molecule characterization of a yeast xylose-H+ symporter" Biochemical Journal, 2006, pp. 543-549, vol. 395.

Leandro, M. J. et al. "The expression in *Saccharomyces cerevisiae* of a glucose/xylose symporter from *Candida intermedia* is affected by the presence of a glucose/xylose facilitator" Microbiology, 2009, pp. 1646-1655, vol. 154.

Leandro, M. J. et al. "Hexose and pentose transport in ascomycetous yeasts: an overview" FEMS Yeast Research, 2009, pp. 511-52, vol. 9.

Lengeler, J. W. et al. "Bacterial PEP-dependent carbohydrate: phosphotransferase systems couple sensing and global control mechanisms" Contributions in Microbiology, 2009, pp. 65-87, vol. 16.

Lindsay, S. E. et al. (1995) "Improved strains of recombinant *Escherichia coli* for ethanol production from sugar mixtures" Applied Micorbiology and Biotechnology, 1995, pp. 70-75, vol. 43.

MacPherson, A. J. S. et al. "Identification of the GalP galactose Transport protein of *Escherichia coli*" Journal of Biological Chemistry, 1983, pp. 4390-4396, vol. 258.

Marsh, D. et al. "Specific spin labeling of the sugar-H+ symporter, GalP, in cell membranes of *Escherichia coli*; site mobility and overall rotational diffusion of the protein" Biochimica and Biophysica Acta, 2001, pp. 464-473, vol. 1510.

(56) References Cited

OTHER PUBLICATIONS

Martin, G. E. M. et al. "Forskolin specifically inhibits the bacterial glactose-H+transport protein, GalP." Journal of Biological Chemistry, 1994, pp. 24870-24877, vol. 269.

Martinez, A. et al. "Low Salt medium for lactate and ethanol production by recombinant *Escherichia coli* B" Biotechnology Letters, 2007, pp. 397-404, vol. 29.

McDonald, T. P. et al. "Asparagine 394 in putative helix 11 of the galactose-H+ symport protein (GalP) from *Escherichia coli* is associated with the internal binding site for cytochalasin B and sugar." Journal of Biological Chemistry, 1997, pp. 15189-15199, vol. 272.

McDonald, T. P. et al. "Cysteine residues in the D-galactose-H+ symport protein of *Escherichai coli*: effects of mutagenesis on transport, reaction with N-ethylmaleimide and antibiotic binding." Biochemical Journal, 2001, pp. 709-717, vol. 353.

Nichols, N. N. et al. "Use of catabolite repression mutants for fermentation of sugar mixtures to ethanol" Applied Microbiology and Biotechnology, 2001, pp. 120-125, vol. 56.

Pao, S. S. et al. "Major facilitator suprefamily" Microbiology and Molecular Biology Review, 1998, pp. 1-34, vol. 62.

Patching, S.G. et al. "Solid-state NMR spectroscopy detects interactions between tryptophan residues of the E. coli sugar transporter GalP and the alpha-anomer of the D-glucose substrate" Journal of American Chemical Society, 2008, pp. 1236-1244, vol. 130.

Patching, S. G. et al. "Relative substrate affinities of wild-type and mutant forms of the *Escherichia coli* sugar transporter GalP determined by solid-state NMR" Molecular Membrane Biology, 2008, pp. 474-484, vol. 25.

Qaidl, S. E. et al. "Repression of galP, the galactose transporter in *Escherichia coli*, requires the specific regulator of N-acetylglucosamine metabolism" Molecular Microbiology, 2009, pp. 146-157, vol. 71.

Runquist, D. et al. (2009) "Expression of the Gxf1 transporter from *Candida intermdia* improves fermentation performance in recombinant xylose-utilizing *Saccharomyces cerevisiae*" Appied Microbiology and Biotechnology, 2009, pp. 123-130, vol. 82.

Saier, M. H. Jr. et al. "Characterization of constitutive galactose permease mutants in *Salmonella typhimurium*" Journal of Bacteriology, 1973, pp. 512-514, vol. 113.

Saloheimo, A. et al. "Xylose transport studies with xylose-utilizing *Saccharomyces cervisiae* strains expressing heterologous and homologous permeases" Applied Microbiology and Biotechnology, 2007, pp. 1041-1052, vol. 74.

Sanchez, A.M. et al. "Efficient succinate production from glucose through over expression of pyruvate carboxylase in an *Escherichia coli* alcohol dehydrogenase and lactate dehydrogenase mutant" Biotechnology Progress. 2005, pp. 358-365, vol. 21.

Zhang, X. et al. "Metabolic evolution of energy-conserving pathways for succinate production in *Escherichia coli*" Proceeding of National Academy of Sciences USA 2009, pp. 20180-20185, vol. 106.

Zhang, X. et al. "Metabolic evolution of energy-conserving pathways for succinate production in *Escherichia coli*" Proceeding of National Academy of Sciences USA 2009, pp. 20180-20185, vol. 106.—Supporting Information pp. 1-6.

* cited by examiner

SEQUENCE LISTING

<160> NUMBER OF SEQ ID NOS: 10

<210> SEQ ID NO 1
<211> LENGTH: 39
<212> TYPE: DNA
<213> ORGANISM: Artificial Sequence
<220> FEATURE:
<223> OTHER INFORMATION: Synthetic Primer.  PCR Primer BY38

<400> SEQUENCE: 1
cagcgtttaa tctatgatga tataactcaa ttattttca                   39

<210> SEQ ID NO 2
<211> LENGTH: 25
<212> TYPE: DNA
<213> ORGANISM: Artificial Sequence
<220> FEATURE:
<223> OTHER INFORMATION: Synthetic Primer.  PCR Primer BY39

<400> SEQUENCE: 2
ggcgataggg agacgggatg ttttc                                  25

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer.  PCR Primer 49a

<400> SEQUENCE: 3
ccgattacac caaccacaac                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer. PCR Primer 49b

<400> SEQUENCE: 4
ggcgaatttc atagctttcc                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer. PCR Primer 50a

<400> SEQUENCE: 5
gaaataggcg ctcacgatta                                        20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer. PCR Primer 50b

<400> SEQUENCE: 6
aaacgtcatt gccttgtttg                                        20

<210> SEQ ID NO 7
<211> LENGTH: 80
<212> TYPE: DNA
<213> ORGANISM: Artificial Sequence

```
<220> FEATURE:
<223> OTHER INFORMATION: Synthetic Primer. PCR Primer 51a

<400> SEQUENCE: 7
taaccatatt ggagggcatc atgcctgacg ctaaaaaaca ggggcggtca aacaaggcaa      60
ctagcgcatg catccattta                                                 80

<210> SEQ ID NO 8
<211> LENGTH: 81
<212> TYPE: DNA
<213> ORGANISM: Artificial Sequence
<220> FEATURE:
<223> OTHER INFORMATION: Synthetic Primer. PCR Primer 51b

<400> SEQUENCE: 8
ctgcaagagg tggcttcctc cgcgatggga ggaagcttgg ggagattaat cgtgagcgcc      60
tggcgaagaa ctccagcatg a                                               81

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer. PCR Primer 17ASPgalP

<400> SEQUENCE: 9
acccagcacg ttttccatca                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer. PCR Primer 18SPgalP

<400> SEQUENCE: 10
tgcgttcaaa ggccagcctc                                                 20
```

METABOLIC EVOLUTION OF *ESCHERICHIA COLI* STRAINS THAT PRODUCE ORGANIC ACIDS

CROSS-REFERENCE TO RELATED APPLICATIONS

The application is the U.S. national stage application of International Patent Application No. PCT/US2010/057111, which claims the priority of the U.S. Provisional Application Ser. No. 61/281,483, filed on Nov. 18, 2009.

GOVERNMENT SUPPORT

This invention was made with United States government support under a contract awarded from the US Department of Energy under Award Number DE-EE0002878/001. The United States government has certain rights in the invention.

The Sequence Listing for this application is labeled "Seq-List.txt" which was created on Nov. 16, 2010 and is 240 KB. The entire content of the sequence listing is incorporated herein by reference in its entirety.

BACKGROUND OF THE INVENTION

A 2004 U.S. Department of Energy report entitled "Top value added chemicals from biomass" has identified twelve building block chemicals that can be produced from renewable feedstocks. The twelve sugar-based building blocks are 1,4-diacids (succinic, fumaric and maleic), 2,5-furan dicarboxylic acid, 3-hydroxy propionic acid, aspartic acid, glucaric acid, glutamic acid, itaconic acid, levulinic acid, 3-hydroxybutyrolactone, glycerol, sorbitol, and xylitol/arabinitol.

Building block chemicals are molecules with multiple functional groups that possess the potential to be transformed into new families of useful molecules. These twelve building blocks can be subsequently converted to a number of high-value bio-based chemicals or materials.

Many natural metabolites derived from biological fermentative processes such as dicarboxylic acids, amino acids, and diols have functional groups that are suitable for polymerization and chemical synthesis of polymers. In the recent years, the efficiency of microorganisms for producing monomeric chemical compounds suitable for industrial usage has been significantly increased through genetic manipulations. However, the cost of producing industrial chemicals through biological fermentative process is still very high. At present the biological fermentative processes for the production of industrial chemicals use purified carbohydrates such as glucose and corn starch as the source of carbon and thereby add cost to the fermentative process for producing industrial chemicals.

The cost of the fermentation process for producing industrial chemicals can be dramatically reduced by using lignocellulosic biomass as the source of carbon in the fermentation process. Lignocellulosic biomass can be obtained from a number of sources including agricultural residues, food processing wastes, wood, and wastes from the paper and pulp industry. Biomass consists of roughly 40-50% of hexose sugars (sugars with six carbon atoms) and 10-30% of pentose sugars (sugars with five carbon atoms). The hexose sugars are known in the art as C6 sugars. The pentose sugars are known in the art as C5 sugars. When hydrolyzed, the lignocellulosic materials yield a mixture of sugars that includes glucose, xylose, arabinose, mannose and galactose. However, a number of fermentation processes for the production of industrial chemicals have been developed with pure glucose as a source of carbon for their growth and metabolism. For example, the *E. coli* strain described in U.S. Pat. No. 7,223,567 uses a rich medium supplemented with glucose as the source of carbon. The *E. coli* strain KJ122 useful for the production of succinic acid described by Jantama et at (2008a; 2008b) and in the published PCT Patent Applications Nos. WO/2008/021141A2 and WO2010/115067A2 can grow on a minimal medium but still requires glucose or another sugar as the source of carbon. It would be ideal if these organisms with the ability to produce industrial chemicals at high efficiency could be grown in a mixture of sugars derived from hydrolysis of lignocellulose. The inventors have discovered a method to enable the microorganisms already optimized to produce a specialty industrial chemical to use a mixture of C5 and C6 sugars derived from hydrolysis of lignocellulosic feedstock.

The ability of the microorganism to use multiple sugars simultaneously is limited by the existence of certain biochemical regulatory systems. These biochemical regulatory systems within the microbial cells have a genetic basis. Efforts have been made to overcome these regulatory systems through genetic manipulations.

In many cases industrial microorganisms are grown in a medium containing glucose or sucrose as the source of carbon. The presence of glucose in the growth medium suppresses the use of other sugars in *E. coli* and other species of industrial microorganisms. The consumption of other sugars such as xylose, a pentose sugar, by these microorganisms is initiated only after glucose in the growth medium has been fully consumed. This phenomenon related to carbon utilization in industrial microorganisms is referred to as catabolite repression or diauxic growth. A method to make the microorganisms co-utilize the different sugars such as C5 and C6 sugars through a relief of catabolite repression during the production of industrial chemicals in a commercial scale would be critical to lowering the cost of industrial chemicals produced by fermentation.

Microorganisms take up sugars through a set of transporter proteins located in the cytoplasmic membrane. The microbial sugar transporters fall within three major categories. The largest group of sugar transporters in bacteria is known as ATP binding cassette (ABC) transporters. As the name implies, the ABC transporters require a molecule of ATP for every molecule of sugar transported into the bacterial cell. XylFGH is an ABC transporter for the transport of xylose, a pentose sugar, into the cell. AraFGH is an ABC transporter for the transport of arabinose, yet another pentose sugar.

The second type of bacterial sugar transporters are grouped under Major Facilitator Super family (MFS). Within the MFS sugar transporters, two different categories of transporter are recognized. MFS includes $H^+$-linked symporters, $Na^+$-linked symporters-antiporters and uniporters. The uniporters are simple facilitators for the sugar transport and do not require a molecule of ATP for every molecule of sugar transported into the cell. The trans-membrane protein Glf in *Zymononas mobilis* is an example of a facilitator. The $H^-$-symporters require an extracellular proton for every sugar molecule transported into the cell. The GalP protein in *E. coli* is a symporter for the transport of galactose, a hexose sugar, into the cell. GalP is a very well characterized symporter with 12 trans-membrane loops. GalP is also reported to have the ability to transport glucose across the cell membrane. AraE is a proton-linked symporter for the transport of arabinose across the cell membrane. Similarly XylE protein is a proton-linked symporter for the transport of xylose.

The third sugar transporter primarily responsible for the uptake of hexose sugars such as glucose is known as the phosphoenolpyruvate: carbohydrate phosphotransferase system (PTS). As a way of differentiating the other two sugar transport systems from PTS, the other two sugar transport systems (ABC transporters and members of MFS transporters) are referred as non-PTS sugar transporters. Transfer of the phosphoryl group from phosphoenolpyruvate (PEP) catalyzed by the PTS drives the transport and phosphorylation of glucose and other sugars and results in the formation of phosphorylated sugars and pyruvic acid inside the cell. PTS generated pyruvic acid is apparently not recycled to PEP under aerobic culture conditions where glucose is the sole source of carbon. Rather, pyruvate is oxidized by way of the tricarboxylic acid cycle to carbon dioxide. Thus, for the transport of every single molecule of glucose, a molecule of PEP is consumed. In terms of cellular bioenergetics, the transport of sugars through PTS is an energy intensive process. Therefore in cells growing anaerobically, where there is a need to conserve the phosphoenolpyruvate content within the cells for the production of industrially useful chemicals, it is desirable to replace the PTS with other non-PTS sugar transporters not requiring a molecule of PEP for every molecule of sugar transported into the cell.

The PTS is comprised of two cytoplasmic components named EI and HPr and a membrane-bound component EII. $E.$ $coli$ contains at least 15 different EII complexes. Each EII component is specific to a sugar type to be transported and contains two hydrophobic integral membrane domains (C and D) and two hydrophilic domains (A and B). These four domains together are responsible for the transport and phosphorylation of the sugar molecules. EI protein transfers the phosphate group from PEP to HPr protein. EII protein transfers the phosphate group from phosphorylated HPr protein to the sugar molecule.

EI is encoded by the ptsI gene. HPr is encoded by the ptsH gene. The glucose-specific EII complex of enteric bacteria consists of two distinct proteins namely, $EIIA^{Glc}$ encoded by the gene crr and the membrane-associated protein $EIICB^{Glc}$ encoded by the gene ptsG. The PTS mediated sugar transport can be inhibited by means of mutating one of these genes coding for the proteins associated with PTS. Functional replacement of PTS by alternative phosphoenolpyruvate-independent uptake and phosphorylation activities (non-PTS) has resulted in significant improvements in product yield from glucose and productivity for several classes of metabolites.

With the decrease in the PTS-mediated glucose uptake, other systems for glucose uptake can be activated to assure the continued availability of glucose within the cell for the production of the industrially useful chemicals. For example, the glf gene coding for glucose permease, a glucose uniporter, has been shown to substitute for the loss of PTS mediated glucose uptake. Similarly the over expression of galP and glk genes are reported to enhance the glucose uptake and phosphorylation in the pts⁻ strain of $E.$ $coli$. GalP is a symporter for the uptake of galactose, a hexose sugar. GalP has been reported to transport glucose in the pts⁻ strain. The significance of GalP mediated glucose uptake is evidenced by the fact that the inactivation of galP gene in the pts⁻ mutant is found to prevent growth on glucose (Yi et al., 2003). In the absence of a PTS, Glk is necessary to achieve the phosphorylation of the glucose molecule before it can enter into glycolysis. The expression of the GalP protein in a pts⁻ stain can be achieved either by expressing the galP gene under a constitutive promoter or by means of relieving the repression of the galP gene expression through mutations in genes coding for the repressor of the galP gene such as galS and galR.

Besides reducing the energy cost incurred in the transport of sugars into the cells, the introduction of a mutations into a gene coding for a protein associated with PTS is expected to relieve the catabolite repression which in turn would allow the simultaneous transport and utilization of all the sugars present in the culture medium including the pentose and hexose sugars. Hernandez-Montalvo et at (2001) studied the utilization of a sugar mixture comprising glucose, arabinose and xylose by an $E.$ $coli$ strain devoid of PTS for the transport of glucose. The pts⁻ mutant was able to uptake sugars by a non-PTS mechanism as rapidly as its wild-type parental strain. In cultures grown in minimal medium supplemented with glucose-xylose or glucose-arabinose mixtures, glucose repressed arabinose or xylose-utilization in the wild type strain. Under the same culture conditions, the pts⁻ mutant co-metabolized glucose and arabinose. However, glucose still exerted a partial repressive effect on xylose consumption. In cultures growing with a triple mixture of glucose-arbinose-xylose, the wild type strain sequentially utilized glucose, arabinose and finally xylose. In contrast, the pts⁻ strain co-metabolized glucose and arabinose, whereas xylose was utilized after glucose-arabinose depletion. As a result of glucose-arabinose co-metabolism, the pts⁻ strain consumed the total amount of sugars contained in the culture medium 16% faster than the wild type strain.

A pts⁻ mutant strain with the capacity to co-metabolize glucose and xylose would cause further increase in the rate of consumption of sugar in the medium leading to an increase in productivity. Thus there is a need in the art for a microorganism that could co-metabolize glucose and xylose since these two sugars represent the predominant sugars that are present in the raw cellulosic hydrolysate. Moreover, it has been reported that the elimination of the ptsG gene function could decrease the rate of growth of microorganisms metabolically engineered to produce organic acids (Sanchez et al., 2005). Therefore there is an additional need to achieve the ability to use multiple sugars simultaneously without compromising the growth rate and rate of production of commercially important chemicals and chemical intermediates.

The objective of the present invention was to metabolically evolve microorganisms capable of producing high levels of industrial chemicals using multiple sugars simultaneously without reducing the productivity. The inventors have surprisingly identified a process for making microorganisms that simultaneously consume multiple sugars through metabolic evolution. This process of metabolic evolution allows the cells to acquire the ability to use multiple sugars without affecting any of its original characteristics such as rapid growth, and the ability to produce specific industrial chemicals at commercially significant quantities.

The inventors have also identified a novel genetic basis for the ability of the microorganism to use glucose and xylose simultaneously. Whole-genome sequencing was used to identify the genetic modification that confers to the microorganisms the ability to use multiple sugars simultaneously in the production of organic acid.

Prior to the present invention, it would have been doubtful whether the ability to utilize both hexose sugars and pentose sugars simultaneously could be accomplished through a simple genetic manipulation. The present invention related to molecular genetics offers the potential to achieve the ability to metabolize efficiently the entire range of biomass-derived sugars. For the first time, the present invention provides a genetic approach for achieving simultaneous glucose and xylose uptake that is not obligately coupled to the expenditure of phosphoenol pyruvate.

BRIEF SUMMARY OF THE INVENTION

We have unexpectedly discovered that the microorganism genetically modified and optimized for producing commercially significant quantities of organic acids through a fermentative process in a minimal growth medium containing glucose as the source of carbon can further be metabolically evolved to use multiple sugars simultaneously as a source of carbon while maintaining the original optimized organic acid production rate.

It is an objective of the present invention to provide a method for conferring to the microorganisms producing organic acid through fermentative process the ability to use multiple types of sugar molecules simultaneously as a source of carbon for their growth and organic acid production. It is another objective of the present invention to provide a fermentation process that produces high yields of organic acids using raw cellulosic hydrolysate.

A feature of the invention is the utilization of the process of metabolic evolution to enable the microorganisms genetically modified and optimized for producing organic acids from glucose to acquire the ability to use hexose and pentose sugars simultaneously.

In one embodiment of the present invention, an *E. coli* bacterium capable of producing an organic acid in a medium with glucose as a source of carbon is metabolically evolved to use additional types of sugar as a source of carbon while maintaining the same rate of organic acid production and retaining the capability to use glucose as a source of carbon.

In a preferred embodiment, the present invention provides an *E. coli* bacterium capable producing organic acid in a minimal growth medium simultaneously using more than one type of sugar.

In yet another preferred embodiment, the present invention provides an *E. coli* bacterium capable of producing organic acid in a minimal growth medium using plant hydrolysate including lignocellulosic hydrolysate as the source of carbon.

In yet another preferred embodiment of the present invention, an *E. coli* bacterium producing succinic acid using glucose and xylose simultaneously is provided.

In yet another preferred embodiment of the present invention, an *E. coli* bacterium producing succinic acid in a minimal growth medium using plant hydrolysate including lignocellulosic hydrolysate is provided.

The present invention is especially useful for producing highly purified organic acids in a very cost-effective manner through biological fermentative process using lignocellulosic materials.

In yet another embodiment, the present invention provides a method for making a microorganism which uses multiple sugars simultaneously by means of mutating the genes coding for non-PTS transporter proteins in addition to reducing the activity of a gene coding for a protein associated with a PTS sugar transporter.

In a more preferred embodiment, a microorganism having PTS sugar transporter with reduced activity and a mutated form of galactose symporter is provided.

Additional advantages of this invention will become readily apparent from the ensuing description.

DETAILED DESCRIPTION OF PREFERRED EMBODIMENTS

Figure 1:
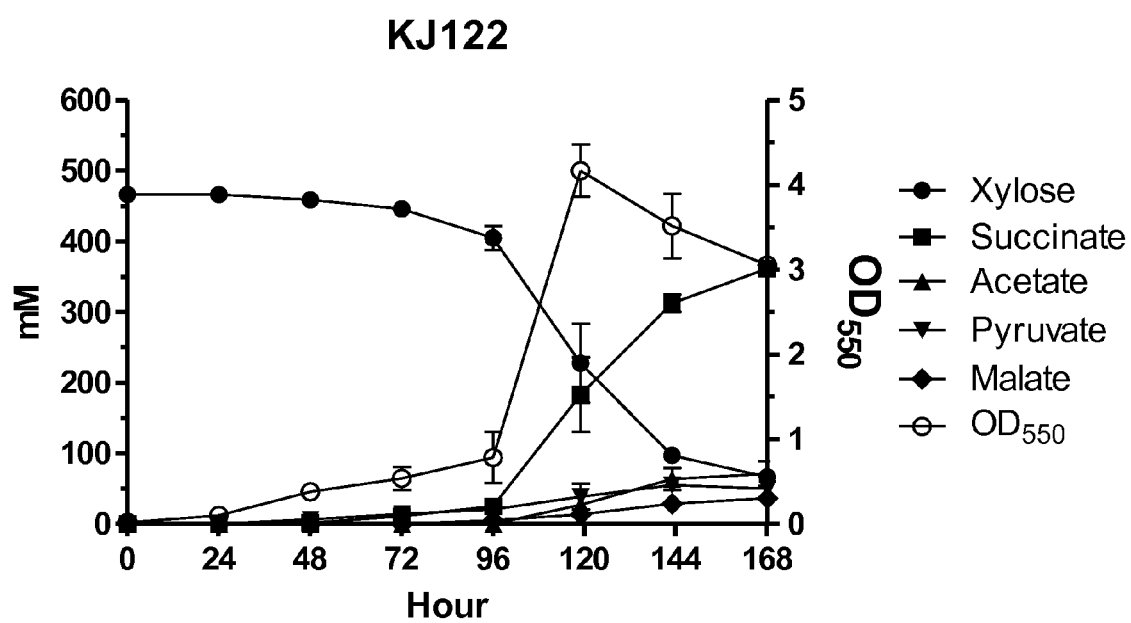
FIG. 1. Fermentation profile for KJ122 strain of *E. coli* in mineral salts medium supplemented with 8% xylose. Fermentation was carried out for a total period of 168 hours. The xylose utilization shown in solid circles started around 96 hours accompanied by an increase in the bacterial cell density measured in terms of an increase in optical density at 550 nm shown in open circles. The increase in succinate concentration shown in solid squares occurred around 96 hours. Also shown in the figure are the changes in the concentration of acetate, pyruvate and malate in the medium during the course of 168 hours of fermentation.

The present invention provides a process for the production of organic acids in commercially significant quantities from the fermentation of carbon compounds by recombinant microorganisms. More specifically, this present invention provides the microorganisms suitable for the production of organic acid through fermentative process. The microorganisms of the present invention possess the ability to use multiple sugars in the fermentative process for the production of commercially significant quantities of organic acid.

Disclosed in this present invention are the microorganisms suitable for the production of succinic acid through fermentative process. Although the present invention provides a process for the production of succinic acid in commercially significant quantities from the carbon compounds by genetically modified bacterial strains, the teachings of the present invention are equally applicable to the industrial production of a number of other chemicals.

For the purpose of the description of the present invention, the following definitions shall be used.

A number of industrially useful chemicals can be manufactured using the present invention. Examples of such chemicals include, but are not limited to, ethanol, butanols, lactate, succinate, fumarate, malate threonine, methionine and lysine. Since organic acids can exist both as free acids and as salts (for example, but not limited to, salts of sodium, potassium, magnesium, calcium, ammonium, chloride, sulfate, carbonate, bicarbonte, etc), chemical names such as succinic acid, fumaric acid, malic acid, aspartic acid, threonine, methionine, and lysine shall be meant to include both the free acid and any salt thereof. Likewise, any salt, such as succinate, fumarate, malate, aspartate, etc., shall be meant to include the free acid as well.

The present invention combines the technique of specific genetic modifications with the process of metabolic evolution to obtain strains showing high yield, titer and volumetric productivity for succinic acid production under anaerobic growth condition in the mineral salt medium with a carbohydrate substrate.

As used in the present invention, the term "titer" means the molar concentration of particular compound in the fermentation broth. Thus in the fermentation process for the production of succinic acid according to the present invention, a succinic acid titer of 100 mM would mean that the fermentation broth at the time of measurement contained 100 mMoles of succinic acid per liter of the fermentation broth.

As used in the present invention, the term "yield" refers to the moles of particular compound produced per mole of the feedstock consumed during the fermentation process. Thus in the fermentative process for the production of succinic acid using glucose as the feedstock, the term yield refers to the number of moles of succinic acid produced per mole of glucose consumed.

As used in the present invention, the term "volumetric productivity" refers to the amount of particular compound in grams produced per unit volume per unit time. Thus a volumetric productivity value of 0.9 g $L^{-1}h^{-1}$ for succinic acid would mean that 0.9 gram succinic acid is accumulated in one liter of fermentation broth during an hour of growth.

As used in the present invention, the term "gene" includes the open reading frame of the gene as well as the upstream and downstream regulatory sequences. The upstream regulatory region is also referred as the promoter region of the gene. The downstream regulatory region is also referred as the terminator sequence region.

The phrase "functionally similar" means broadly any wild type or mutated DNA sequence, gene, enzyme, protein, from any organism, that has a biological function that is equivalent or similar to any wild type or mutated DNA sequence, gene, enzyme, protein that is found in the same or a different organism by the methods disclosed herein. Functionally similarity need not require sequence homology. Allele is one of two or more forms of DNA sequence of a particular gene. Each gene has different alleles. A gene without any mutation is referred as a wild type allele when compared to a corresponding gene that has a mutation.

A homolog is a gene related to a second gene by descent from a common ancestral DNA sequence. The term, homolog, may apply to the relationship between genes separated by the event of speciation or to the relationship between genes separated by the event of genetic duplication. Orthologs are genes in different species that evolved from a common ancestral gene by speciation. Normally, orthologs retain the same function in the course of evolution. Identification of orthologs is critical for reliable prediction of gene function in newly sequenced genomes. Speciation is the origin of a new species capable of making a living in a new way from the species from which it arose. As part of this process it has also acquired some barrier to genetic exchange with the parent species. Paralogs are genes related by duplication within a genome. Orthologs retain the same function in the course of evolution, whereas paralogs evolve new function, even if these are related to the original one.

A gene or protein with "altered activity" is broadly defined as gene or protein that produces a measurable difference in a measurable property when compared to the relevant wild type gene or protein. The altered activity could manifest itself in a general way by increasing or decreasing the growth rate or efficiency of succinate production of the strain containing the altered gene or protein. Other measurable properties include, but are not limited to enzyme activity, substrate specificity of an enzyme, kinetic parameters of an enzyme such as affinity for a substrate or rate, stability of an enzyme, regulatory properties of an enzyme, gene expression level, regulation of gene expression under various conditions, etc.

As used in the present invention, the term mutation refers to genetic modifications done to the gene including the open reading frame, upstream regulatory region and downstream regulatory region. The gene mutations result either in an up regulation or a down regulation or complete inhibition of the transcription of the open reading frame of the gene. The gene mutations are achieved either by deleting the entire coding region of the gene or a portion of the coding nucleotide sequence or by introducing a frame shift mutation, a missense mutation, and insertion, or by introducing a stop codon or combinations thereof. Mutations may occur in the structural genes coding for the proteins directly involved in the biological functions such as enzyme reactions or transport of the organic molecules across the cell membrane. Alternately, mutations may occur in the regulatory genes coding for the proteins which control the expression of the genes coding for the proteins directly involved in the biological functions. The proteins which control the expression of the other genes are referred as regulatory proteins and the genes coding for these regulatory proteins are referred as regulatory genes.

"Mutation" shall also include any change in a DNA sequence relative to that of the relevant wild type organism. For example, a mutation found in strain KJ122 is any change in a DNA sequence that can be found when the DNA sequence of the mutated region is compared to that of the parent wild type strain, *E. coli* C, also known as ATCC 8739. A mutation can be an insertion of additional DNA of any number of base pairs or a deletion of DNA of any number of base pairs. A particular type of insertion mutation is a gene duplication. A gene can be duplicated by a spontaneous mutational event, in which the second copy of the gene can be located adjacent to the original copy, or a gene can be duplicated by genetic engineering, in which the second copy of the gene can be located at a site in the genome that is distant from the original copy. A mutation can be a change from one base type to another base type, for example a change from an adenine to a guanine base. In the vernacular of genetics, a mutation can be a missense (which changes the amino acid coded for by a codon), a nonsense (which changes a codon into stop codon), a frameshift (which is an insertion or deletion of a number of bases that is not a multiple of three and which changes the reading frame and alters the amino acid sequence that is encoded downstream from the mutation, and often introduces a stop codon downstream from the mutation), or an inversion (which results from a DNA sequence being switched in polarity but not deleted).

A "null mutation" is a mutation that confers a phenotype that is substantially identical to that of a deletion of an entire open reading frame of the relevant gene, or that removes all measurable activity of the relevant gene.

A "mutant" is a microorganism whose genome contains one or more mutations.

As used in this invention, the term "exogenous" is intended to mean that a molecule or an activity derived from outside of a cell is introduced into the host microbial organism. In the case an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred as homologous DNA. If the nucleic acid derived from a different microbial species, it is referred as heterologous DNA. Irrespective of the nature of the DNA, whether it is homologous or heterologous, when introduced into a host cell, the DNA as well as the activity derived form that introduced DNA is referred as exogenous. Therefore, exogenous expression of an encoding nucleic acid of the invention can utilize either or both heterologous and homologous encoding nucleic acid.

A cell that "utilizes C5 and C6 sugars simultaneously" means a cell that consumes at a measurable rate, and without any substantial delay at the beginning of an inoculation of said cell into a medium, both a C5 sugar, such as xylose, arabinose, ribose, etc., and a C6 sugar, such as glucose, fructose, galactose, etc., when the cell is grown in a medium that contains a substantial concentration of both a C5 and a C6 sugar. The medium containing both a C5 and a C6 sugar can be made from purified sugars, or it can be derived from a biomass hydrolysate.

A number of microorganisms including *Escherichia coli, Citrobacter freundii, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa,*

Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri, Klebsiella oxytoca, Klebsiella pneumonia or Xanthomonas citri are suitable for the present invention. The recombinant microorganisms most suitable for this present invention are derived preferably from the Enterobacteriaceae family. The preferred microorganisms are selected form the genera Escherichia, Erwinia, Providencia, Klebsiella, Citrobacter and Serratia. The genus Escherichia is most preferred. Within the genus Escherichia, the species Escherichia coli is particularly preferred.

E. coli strains capable of producing organic acids in significant quantities are well known in the art. For example, the U. S. Patent Application Publication No. 2009/0148914 provides strains of E. coli as a biocatalyst for the production of chemically pure acetate and/or pyruvate. The U.S. Pat. No. 7,629,162 provides derivatives of E. coli K011 strain constructed for the production of lactic acid. International Patent Applications published under the Patent Cooperation Treaty Nos. WO 2008/115958 and WO 2010/115067 provide microorganism engineered to produce succinate and malate in a minimal mineral salt medium containing glucose as a source of carbon in a pH-controlled batch fermentation.

The wild type E. coli strains obtained from culture collections such as the ATCC (American Type Culture Collection) can be genetically engineered and subsequently metabolically evolved to obtain a strain with an enhanced ability to produce one more organic acid in commercially significant amounts.

The term "genetically engineered" or "genetic engineering" as used herein refers to the practice of altering the expression of one or more enzymes in the microorganisms through manipulating the genomic DNA or a plasmid of the microorganism. The genomic manipulations involve either altering, adding or removing specific DNA sequences from the genomic DNA. The genetic manipulations also involve the insertion of a foreign DNA sequence into the genomic DNA sequence of the microorganism. In the most preferred embodiments of the present invention, the genetic manipulations are accomplished by means of removing specific DNA sequences from the genomic DNA of the microorganisms without introducing any foreign DNA. Certain genetic manipulations necessary to inactivate the expression of a gene coding for a particular protein product requires an insertion of a foreign DNA sequence into the genome of the microorganism. In the most preferred embodiment of the present invention, the introduced exogenous DNA sequences are ultimately removed from the genomic DNA of the microorganism so that the microorganism at the end of the genetic engineering process would have no exogenous DNA in its original genomic DNA. Various techniques necessary for accomplishing the objectives of the preferred embodiment of the present invention have been described in detail in Jantama et at (Biotechnology and Bioengineering 99: 1140-1153 and Biotechnology and Bioengineering 101: 881-893). The published U.S. Pat. No. 7,629,162 and U. S. Patent Application 2009/0148914 and the International patent applications published under the Patent Cooperation Treaty with International Publication Numbers WO 2008/115958 and WO 2010/115067 also describe the genetic engineering techniques useful in practicing various embodiments of this present invention. These scientific publications as well as patent documents are herein incorporated by reference for the purpose of providing the details for genetic engineering techniques useful for the present invention.

The microorganisms suitable for the practice of present invention can be grown aerobically (in the presence of oxygen) or anaerobically (in the complete absence of oxygen) or micro aerobically (with a low rate of oxygen supply). Alternatively, the microorganisms suitable for the present invention can be grown in a dual-phase growth regime, wherein the microorganism is initially grown in aerobic growth condition to reach a certain level of cell growth before transferring it to anaerobic growth condition to achieve the production of desired organic acids in commercially significant quantities. In order to make the microorganism to produce a particular organic acid, various enzymes involved in a number of microbial metabolic pathways including glycolytic pathway, tricarboxylic acid cycle (also called Krebs cycle or TCA cycle) and glyoxylate stunt can be manipulated by a variety of genetic engineering techniques described in the scientific and patent literature cited and incorporated by references in the paragraph above. All of those references are incorporated into this patent application by reference. The details about various microbial metabolic pathways can be found in the standard biochemistry text books such as Principles of Biochemistry, by Lehninger and Biochemistry by Lubert Stryer.

Depending on the type of organic acid preferred, the metabolic pathways are genetically engineered so that a microorganism produces a particular organic acid of our choice. The microorganisms are capable of synthesizing a number of organic acids including lactic acid, acetic acid, and succinic acid. The list of the enzymes that are active in the microbial fermentative pathway which can be manipulated using the known genetic engineering techniques includes, but is not limited to, isocitrate synthetase (aceA), malate synthase (aceB), the glyoxylate shunt operon (aceBAK), acetate kinase-phosphotransacetylase (ackA-pta); aconitase hydratase 1 and 2 (acnA and acnB); acetyl-CoA synthetase (acs); alcohol dehydrogenase (adhE); citrate synthase (citZ); fumarate reductase (frd); lactate dehydrogenases (ldh); malate dehydrogenaase (mdh); aceBAK operon repressor (iclR); phosphoenol pyruvate carboxlase (pepC); pyruvate formate lyase (pfl); pyruvate oxidase (poxB); and pyruvate carboxylase (pyc). Besides these genes directly involved in the glycolysis, tricarboxylic acid cycle and glyoxylate stunt of microbial metabolic pathways, genetic manipulation of the genes involved in the uptake of carbon compounds useful as a source of energy for the synthesis of organic acid can also be manipulated either to enhance the carbon uptake or to enhance the efficiency of energy utilization in organic acid production. For example a decrease in the glucose uptake by a phosphotransferase system (PTS) could help in reducing the energy spent on glucose uptake into the microbial cell. The energy conserved by manipulating the PTS can be channeled to improve the efficiency of organic acid production. The phosphotransferase system genes ptsH and ptsG can be manipulated to conserve the energy in glucose uptake and thereby improve the efficiency of organic acid production by microorganism. Thus by mining the data available in the area of microbial metabolic pathways, one can delete a set of genes so as to block most of the metabolic pathways and channel the carbon flow to the production of a particular organic acid.

Besides the central metabolic pathways and the sugar uptake mechanisms, the carboxylating enzymes within the bacterial cells can also be manipulated to improve the fermentative production of organic acid. The role of carboxylating enzymes in the fermentative production is now well established. At least four different types of carboxylating enzymes are known to be functional within bacterial cells. The phosphoenol pyruvate carboxylase (PEPcase or PPC) carboxylates phosphoenol pyruvate leading to the formation of oxaloacetic acid. The malic enzymes carboxylate pyruvic acid leading to the formation of malic acid and requires reduced cofactors such as NADH or NADPH. The third carboxylating enzyme known as pyruvate carboxylase (PYC) carboxylates pyruvic acid to produce oxaloacetic acid. The fourth carboxylating enzyme known as phosphoenolpyruvate carboxykinase (PCK) carboxylates phosphoenol pyruvate to oxaloacetate with the production of one molecule of ATP for every molecule of oxaloacetate produced from the carboxylation of phosphoenol pyruvate molecule. Any one of these carboxylating enzyme can also be manipulated appropriately in the bacterial strains with the ability to utilize hexose and pentose sugars simultaneously to improve the fermentative production of industrially useful chemicals.

The phosphoenolpyruvate carboxykinase (pck) can be genetically manipulated to improve the flow of carbon into the tricarboxylic acid cycle. The advantage in improving the activity of pck lies in the fact that this enzyme while carboxylating phosphoenol pyruvate to oxaloacetate, results in the production of a molecule of ATP for every molecule of oxaloacetate produced. An increase in the ATP yield would increase the growth rate of the cells.

The recruitment of the native pck for fermentative succinate production can be achieved by any mutation that positively affects the transcription of the pck gene. An increase in the level of PCK activity can be achieved by means of expressing the pck gene in a multicopy plasmid with a native promoter or any other promoter sequence which is known to increase the gene's expression. Another way to increase the expression of the pck gene within the cell is to integrate additional copies of the pck gene using transposons. In another embodiment of the present invention, the native promoter of the pck gene can be replaced by some other promoter elements known to enhance the level of activity. An increased expression of pck gene can also be achieved either by mutation in the promoter region of the gene or by genetic manipulation of the regulatory elements that are known to interact with the promoter region of the pck gene. The gene coding for a regulator protein of the pck gene can be mutated or deleted or overexpressed in some way in order to increase the expression of pck gene. A single point mutation (G to A transition at position −64 relative to the ATG start codon of pck gene) could increase the transcription of the pck gene accompanied by a corresponding increase in the phosphoenol pyruvate carboxykinase enzyme activity. A similar increase in the pck gene expression can also be achieved by genetically manipulating the genes coding for the proteins known to regulate the expression of pck gene.

The production of the organic acid by the genetically engineered microorganism can be confirmed and quantified by using appropriate techniques well known in the art. For example, HPLC techniques can be used to measure the quantity of the organic acid produced by the selected clone. The HPLC technology is also helpful in determining the purity of the organic acid produced by the selected clones.

The microbial organism of the present invention can be grown in a number of different culture media well known in the field of microbiology. For example, the wild type and mutant strains of E. coli are grown in Luria-Bertani (LB) medium containing 1% (w/v) tryptone, 0.5% (w/v) yeast extract, and 0.5% (w/v) NaCl. For the commercial production of the organic acid using fermentative process involving genetically modified microorganism as biocatalyst, a minimal mineral salt medium supplemented with a carbon source is preferred. The use of a minimal mineral salt medium as opposed to a rich medium like LB medium reduces the cost for the production of organic acids in a commercial scale. The minimal mineral mediums suitable for the present invention include NBS medium (Causey et al., 2007) and AM1 medium (Martinez et al., 2007). The NBS medium contains 1 mM betaine, 25.72 mM $KH_2PO_4$, 28.71 mM $K_2HPO_4$, 26.50 mM $(NH_4)_2HPO_4$, 1 mM $MgSO_4.7H_2O$, 0.1 mM $CaCl_2.2H_2O$, 0.15 mM Thiamine HCl, 5.92 µM $FeCl_3.6H_2O$, 0.84 µM $CoCl_2.6H2O$, 0.59 µM $CuI_2.2H_2O$, 1.47 µM $ZnCl_2$, 0.83 µM $Na_2MoO_4.2H_2O$, and 0.81 µM $H_3BO_3$. The AM1 medium contains 1 mM betaine, 19.92 mM $(NH_4)_2HPO_4$, 7.56 mM $NH_4H_2PO_4$, 1.5 mM $MgSO_4.7H2O$, 1.0 mM Betaine-KCl, 8.88 µM $FeCl_3.6H_2O$, 1.26 µM $CoCl_2.6H_2O$, 0.88 µM $CuCl_2.2H_2O$, 2.20 µM $ZnCl_2$, 1.24 µM $Na_2MoO_42H_2O$, 1.21 µM $H_3BO_3$ and 2.50 µM $MnCl_2.4H_2O$.

Since the accumulation of organic acids in the growth medium tends to decrease the pH of the medium, it is necessary to add appropriate neutralizing agents as required to the culture medium. The pH of the culture vessel can be continuously monitored using a pH probe, and appropriate base can be added to maintain the pH of the growth medium around neutral pH. The bases suitable for maintaining the pH of the microbial culture includes, NaOH, KOH, $NH_4HCO_3$, $Na_2CO_3$, $NaHCO_3$, $K2CO_3$ and $(NH_4)_2CO_3$. The bases suitable for this purpose can be used alone or in combination.

The mineral medium for microbial growth is supplemented with a carbon source. The carbon sources useful in the present invention include but are not limited to pentose sugars like xylose, and hexose sugars like glucose, fructose, and galactose. The carbon source can also be satisfied by providing a combination of different sugars such as a combination of glucose and xylose. The carbon source can also be derived from a hydrolysis of starch or lignocellulose. The hydrolysis of complex carbohydrates such as starch and lignocelluloses can be achieved either by using thermo-chemical conversion processes or enzymatic methods well known in the art. The preferred carbon source for the industrial production of organic acid using microbial fermentation is lignocellulosic hydrolysate derived from the hydrolysis of agricultural or forestry wastes. The lignocellulosic hydrolysate may further be fractionated to yield a hexose-enriched and a pentose-enriched fraction and those fractions can serve as the source of carbon for the commercial production of the organic acids using microbial fermentation process. The lignocellulosic hydrolysate can further be detoxified to remove certain chemicals such as furfural which are found to be toxic to a number of microbial organisms above certain concentrations.

The microbial strains obtained from genetic engineering have the expected genotype for the production of organic acids. However, their growth rate in the minimal mineral salt medium or the their ability to produce specific organic acid at the required rate or their ability to tolerate certain chemicals in the carbon source derived from lignocellulosic hydrolysate may not be suitable for using these genetically modified microorganism as a biocatalyst for the commercial production of organic acid through large scale fermentation process. Genetically modified microbial strains obtained from gene deletions are subsequently selected for the best representative clone via metabolic adaptation or evolution. During the metabolic evolution, the selected culture is repeatedly transferred into fresh minimal medium for a period of time to achieve a clone in which one or more spontaneous mutations that occurred during selection results in a phenotype that exhibits fast cell growth, rapid consumption of different carbon sources, ability to use multiple sugars simultaneously, ability to tolerate toxic chemicals in the carbon source and high production yield and productivity of the desired organic acid, but low production of other organic acids. During the metabolic evolution, attention is paid to select the clone with the desirable phenotypes. A microbial organism genetically engineered to produce a particular organic acid may not have a commercially attractive growth rate and consequently may not show the expected yield of that particular organic acid. Metabolic evolution can be followed to evolve a strain which shows a significant growth accompanied by an increased rate for the production of that particular organic acid. A clone resulting from the metabolic evolution showing a very good growth rate in mineral medium supplemented with a carbon source but that has not improved in the yield of the desired organic acid is not a desirable clone.

The KJ122 strain of E. coli is used in the preferred embodiment of the present invention. KJ122 was derived from the wild type E. coli C strain through multiple stages involving a combination of both genetic engineering and metabolic evolution. Using genetic engineering techniques twelve different genes including lactate hydrogenase (ldhA), alcohol dehydrogenase (adhE), formate transporter (focA), acetate kinase (ackA), pyruvate-formate lyase (pflB), methylglyoxal synthase (msgA), pyruvate oxidase (poxB), propionate kinase with acetate kinase activity (tdcD), α-ketobutryate formate lyase (tdcE), citrate lyase (citF), aspartate aminotransferase (aspC), and malic enzyme (sfcA) were deleted from the chromosomal DNA of the parent E. coli C strain ATCC 8739. The genetic manipulations done to E. coli C strain ATCC 8739 leading to the KJ122 strain have been described in detail by Jantama et al (2008a 2008b).

During the process of metabolic evolution using selective pressure to force the organism to acquire a desirable phenotype, two possible changes could occur. The organism could simply adapt itself to the selective pressure and show a changed phenotype. Alternatively, the organism might undergo certain genetic changes under selective pressure and exhibit a changed phenotype permanently. When there was only an adaptation and there is no genetic change, the organism reverts back to its original phenotype once the selection pressure is relieved. These organisms are referred to as "adapted" organisms. The "adapted" microorganisms have to undergo another fresh round of metabolic evolution under selection pressure to show a changed phenotype. On the other hand, when there is an accompanying genetic change, the changed phenotype will continue to exist even when there is no selection pressure. Metabolic evolution accompanied by a certain genetic change is desirable. The microorganism acquiring a stable genetic change during metabolic evolution can be easily identified by means of growing the microorganism in the original growth medium without any selection pressure for some time before transferring it to the fresh medium with the selection pressure. If these organisms are able to show good growth and the expected phenotype without any lag period, the organism is considered to have acquired a changed genotype during metabolic evolution.

The basis of genetic change gained during the metabolic evolution can be determined by sequencing the chromosomal DNA of the organism and comparing the sequence data with that of the parent strain. The genomic sequence data can be obtained by means of following the techniques well known in the art. Thus, the parent stain KJ122 obtained from E. coli strain ATCC 8739 can be subjected to metabolic evolution to obtain a strain with a desirable new phenotype. The genome of the metabolically evolved new strain along with the parent strain KJ122 can be sequenced and the mutations in the metabolically evolved strain accounting for the changed phenotype can be identified.

As defined in this invention, the term mutation includes any change in the nucleotide sequence within the gene. A nucleotide change within a gene may be a single nucleotide change within a triplet codon leading to the replacement of one amino acid residue with another amino acid residue. Alternately, a nucleotide change within an open reading frame of a gene may involve a deletion of a portion of the open reading frame or the entire open reading frame. A nucleotide change within an open reading frame can also include introduction of a stop codon and as a result, the open reading frame codes for a truncated protein instead of a full-length protein. As used in the present invention the term mutation also includes changes in the nucleotide sequences in the upstream or downstream of the open reading frame. The regions upstream and downstream of an open reading frame contain several regulatory nucleotide sequences and are involved in the expression of the protein coded by the open reading frame. A mutation occurring in these regulatory regions can alter the gene expression leading either to an up-regulation or down-regulation of gene function. Another possibility is a nucleotide insertion or deletion resulting in a frames shift mutation.

Based on the knowledge gained from the present invention, the genetic modifications leading to the simultaneous utilization of pentose and hexose sugars can be carried out in any bacterial strain already genetically engineered for the production of one or more industrial chemicals using glucose as the source of carbon. Alternately, the genetic modification required for the simultaneous utilization of hexose and pentose sugar can be carried out in any wild type bacterial strains and the wild type bacterial strain thus modified for simultaneous hexose and pentose sugar utilization can be subjected to further genetic modifications to develop a microorganism suitable for the production of industrial chemicals in a commercial scale.

EXPERIMENTAL SECTION

General Remarks

Strain and inoculum preparations: KJ122 (E. coli C, ΔldhA, ΔadhE, ΔackA, ΔfocA-pflB, ΔmgsA, ΔpoxB, ΔtdcDE, ΔcitF, ΔaspC, ΔsfcA) was used in the present invention. KJ122 was derived from E. coli C (ATCC 8739) strain through genetic modifications as described by Jantama et at (2008a; 2008b) and in the International Patent Applications published under Patent Cooperation Treaty with International Publication Nos. WO 2008/115958 and WO 2010/115067. All these documents are herein incorporated by reference.

E. coli strain KJ122 is capable of fermenting 10% glucose in AM1 mineral media to produce 88 g/L succinate, normalized for base addition, in 72 hours. AM1 medium contains 2.63 g/L $(NH_4)_2HPO_4$, 0.87 g/L $NH_4H_2PO_4$, 1.5 mM $MgSO_4$, 1.0 mM betaine, and 1.5 ml/L trace elements. The trace elements are prepared as a 1000× stock and contained the following components: 1.6 g/L $FeCl_3$, 0.2 g/L $CoCl_2.6H_2O$, 0.1 g/L $CuCl_2$, 0.2 g/L $ZnCl_2.4H_2O$, 0.2 g/L $NaMoO_4$, 0.05 g/L $H_3BO_3$, and 0.33 g/L $MnCl_2.4H_2O$. The pH of the fermentation broth is maintained at 7.0 with: 1:4 (6 N KOH: 3 M $K_2CO_3$) (1.2 N KOH, 2.4 M $K_2CO_3$).

In some experiments, corn steep liquor was added. It is a byproduct from the corn wet-milling industry. When compared to the yeast extract and peptone, it is an inexpensive source of vitamins and trace elements.

Fermentations:

Fermentations were started by streaking on a fresh NBS-2% xylose plate a glycerol stock of E. coli strain genetically engineered to produce succinic acid and stored in the −80° C. freezer. After 16 hours (37° C.), cells from the plate were scraped off and inoculated directly into the fermentation vessel. The fermentation vessels have a working volume of 350 ml. This first fermentation was referred to as the "seed" culture, and was not used to accumulate data. The medium in all fermentations was traditional AM1 medium supplemented with 0.03M $KHCO_3$, 1 mM betaine and 8% xylose (unless otherwise noted) and neutralized with a base consisting of 1.2 N KOH and 2.4 M $K_2CO_3$. The fermentation vessels were maintained at a pH of 7.0, 37° C. with 150 rpm stirring. After 24 hours, the seed culture was used to inoculate a new culture (whether batch experiments or "transfers") to a starting $OD_{550}$ of 0.05. With the exceptions of the daily transfers, all experiments were conducted in triplicate. The C5/C6 co-fermentation experiment included 4% xylose, 7% glucose, 0.5% arabinose, 0.4% galactose, and 0.3% mannose (pure sugars) and was inoculated from a culture growing on xylose as the sole carbon source and 0.08% furfural. The C5/C6 co-fermentation was also conducted with the mixture of 8% xylose and 1% glucose. These experiments were conducted in triplicate without addition of inhibitors, with 1% acetate or with 0.1% furfural.

Cell Growth:

Cell mass was estimated by measuring the optical density at 550 nm ($OD_{550}$) using a Thermo Electronic Spectronic 20 spectrophotometer.

Organic Acid and Sugar Analysis:

The concentration of various organic acids and sugars were measured by HPLC. Succinic acid and other organic acids present in the fermentation broth were analyzed on Agilent 1200 HPLC apparatus with BioRad Aminex HPX-87H column. BioRad Microguard Cation $H^+$ was used as a guard column. The standards for HPLC analysis were prepared in 0.008N sulfuric acid. The HPLC column temperature was maintained at 50° C. Sulfuric acid at 0.008N concentration was used as a mobile phase at the flow rate of 0.6 ml/min. Quantification of various components was done by measuring their absorption at 210 nm.

Metabolic Evolution:

Cells from the pH controlled fermentations were serially transferred at 24 hours to encourage metabolic evolution though growth-based selection. The inoculum, approximately 1/100 of the volume of new media, was added directly to pre-warmed, fresh media to a starting $OD_{550}$ of 0.05. Clones with improved fermentation characteristics were isolated. The metabolic evolution strategy was applied to improve xylose fermentation.

Preparation of Bagasse:

Sugarcane bagasse is obtained from sugar mills in Florida which is a waste product that is typically used by burning for energy. This waste product is used as the starting material for the preparation of hemi-cellulose and cellulose fractions using dilute acid pretreatment.

The sugarcane bagasse is dried to a moisture content of about 10% and milled using a knife mill. The material is treated in steam reactors (Zipperclave & Parr) with dilute sulfuric acid at moderate temperatures. Typical pretreatment conditions for dilute acid pretreatment are 0.1-3% acid concentration, 100-200° C. temperature, and 1-30 minutes residence time in the reactor. The optimal reactor conditions to achieve maximum xylose yield with minimal sugar degradation are about 0.5% acid concentration, 160° C., and 10 min resident time in the reactor.

PCR and DNA Sequencing:

A set of two galP specific primers BY38 and BY39 (Table 1), were used to obtain the galP gene from TG400, KJ122, and WG37 strains of *E. coli*. The PCR was carried out using the standard protocol using 2phusion HF master mix kit from New England Biolabs. The PCR products were run on a 0.8% agarose gel to determine the size of the PCR products from each of these different strains of *E. coli*. The PCR products were also sequenced using the Sanger method by Tufts DNA sequencing core facility in Boston, Mass., USA. The sequence data were analyzed using the Vector NTI software program.

Construction of WG37 Strain of *E. coli*:

WG37 stain of *E. coli* was derived from KJ122 strain by deleting the entire coding region of the galP gene. The galP gene was deleted in two steps involving homologous recombination. In the first stage, the galP gene sequence was replaced by a cassette containing an antibiotic marker and sacB gene sequence. The recombinants were selected on a LB plate with antibiotic. In the second stage, the antibiotic cassette was removed from the chromosomal DNA and the recombinants were selected on a medium containing sucrose. The colonies growing on the sucrose containing plates are highly enriched for loss of the sacB cassette.

In the construction of the WG37 strain of *E. coli*, a kan cassette was amplified by PCR using the primers 51a and 51b (Table 1) and XmnI digested pGW162 plasmid as a template. The DNA fragment of kan-sacB cassette was introduced into KJ122 strain of *E. coli*. In the first step, transformants were selected on a LB plate with kanamycin and were confirmed by PCR using the primers 49a, 49b (Table 1). This strain was designated as WG35. The galP gene and neighboring 300 bp regions were amplified using the primers 49a, 49b (Table 1) and cloned into pGEMT easy vector to produce plasmid pGW180. Diluted preparation of this plasmid DNA served as a template for inside-out amplification using the primers 50a, 50b (Table 1). The resulting fragment was self ligated to construct plasmid pGW181. In pGW181 (Table 1), the galP gene was deleted. The DNA fragment containing the galP deletion was amplified by PCR with the primers 49a, 49b and the plasmid pGW181 as template. The PCR product was introduced into WG35 and the transformants were selected on LB plates with 10% sucrose. Resulting clones were tested for loss of kanamycin resistance. The final galP deletion strain was designated as WG37 and the specific gene deletion was confirmed by PCR using primers 49a, and 49b (Table 1).

Example 1

C5 Utilization

*Escherichia coli* strain KJ122 (*E. coli* C, ΔldhA, ΔadhE, ΔackA, ΔfocA-pflB, ΔmgsA, ΔpoxB, ΔtdcDE, ΔcitF, ΔaspC, ΔsfcA) was able to grow aerobically on glucose, xylose, and arabinose. The objective of the present invention was to grow the KJ122 strain of *E. coli* microaerobically in a medium containing both hexose and other pentose sugars and to select an organism that is able to use both types of sugars simultaneously.

Initial screening for C5 utilization was conducted by aerobic growth on NBS mineral medium plates supplemented with 2% of xylose. The plates were incubated at 37° C. overnight. The colonies appearing on the xylose plate were streaked on fresh plates for three consecutive times. At the end of the third transfer on solid NBS mineral medium with 2% xylose, the cells from the plate were scraped off and inoculated directly to a fermentation flask containing AM1 mineral medium supplemented with 0.03 M $KHCO_3$, 1 mM betaine and 8% xylose. The fermentation medium was neutralized with a base consisting of 1.2 N KOH and 2.4 M $K_2CO_3$ to maintain the pH of 7.0 at 37° C. The culture was stirred with a magnetic stir bar operating at the speed of 150 rpm. The liquid culture was grown for an initial period of 24 hours and used as a seed culture to start a new culture with an initial $OD_{550}$ of 0.05.

This culture in the AM1 mineral medium with xylose exhibited an initial 72 hour lag phase during which no growth of KJ122 was noticed. At the end of this initial lag period, KJ122 strain started showing growth. Along with the growth of the bacterial cells as measured by an increase in the OD at 550 nm, there was a decrease in the concentration of xylose in the medium accompanied by a proportional increase in the concentration of the succinic acid in the growth medium.

At the end of the 216 hour growth period in xylose containing medium, a glycerol stock of this culture was prepared and stored at −80° C. Either the fresh culture at the end of the 216 hour growth period or the glycerol stock of the culture prepared at the end of 216 hour growth period was used to inoculate a fresh fermentation vessel with AM1 mineral medium supplemented with 8% xylose. Irrespective of the source of inoculum, whether it was from a fresh culture or a glycerol stock, the culture in the second fermentation vessel grew without any lag period. The succinic acid production also accompanied the bacterial growth without any lag period. Thus three rounds of growth on a solid mineral medium with 2% xylose followed by a single growth cycle for 216 hour period resulted in the "adapted strain" of KJ122 which is able to grow microaerobically on xylose containing medium.

Example 2

Metabolic Evolution of KJ122

In another embodiment of the present invention, the KJ122 strain was subjected to metabolic evolution. The KJ122 culture growing microaerobically in a liquid AM1 medium supplemented with xylose sugar was transferred to a fresh liquid AM1 medium containing 8% xylose every 24 hours for a period of 2 weeks. At the end of these multiple transfers, the KJ122 strain was transferred to a fresh fermentor with AM1 medium supplemented with 8% xylose. The anaerobic growth rate of KJ122 in the fermentor as well as the succinic acid production and the kinetics of xylose utilization were monitored. The succinic acid production in the fermentor started immediately without any lag period and also produced higher final titers and this strain is referred as a "metabolically evolved strain." In our strain collection, this metabolically evolved strain has been designated as TG400.

In order to determine whether the "adapted strain" of KJ122 and the "metabolically evolved" TG400 strain have any genetic basis for their changed phenotype, the following experiments were carried out. The unmodified KJ122 strain, the "adapted strain of KJ122" and the "metabolically evolved" TG400 strain were streaked onto a plate with fresh mineral medium containing 2% glucose. The resulting colonies were streaked onto a fresh plate with 2% glucose. This streaking was done on a daily basis for 11 consecutive days. At the end of the eleventh day, the culture was streaked onto an agar plate containing xylose. The colonies growing on the xylose plate were streaked again onto a fresh xylose containing plate. This was followed by the transfer of the colonies growing on the second xylose containing plate to a liquid culture. The growth rate, succinic acid production kinetics and the rate of decease in the concentration of the xylose in the culture medium were monitored.

Figure 2:
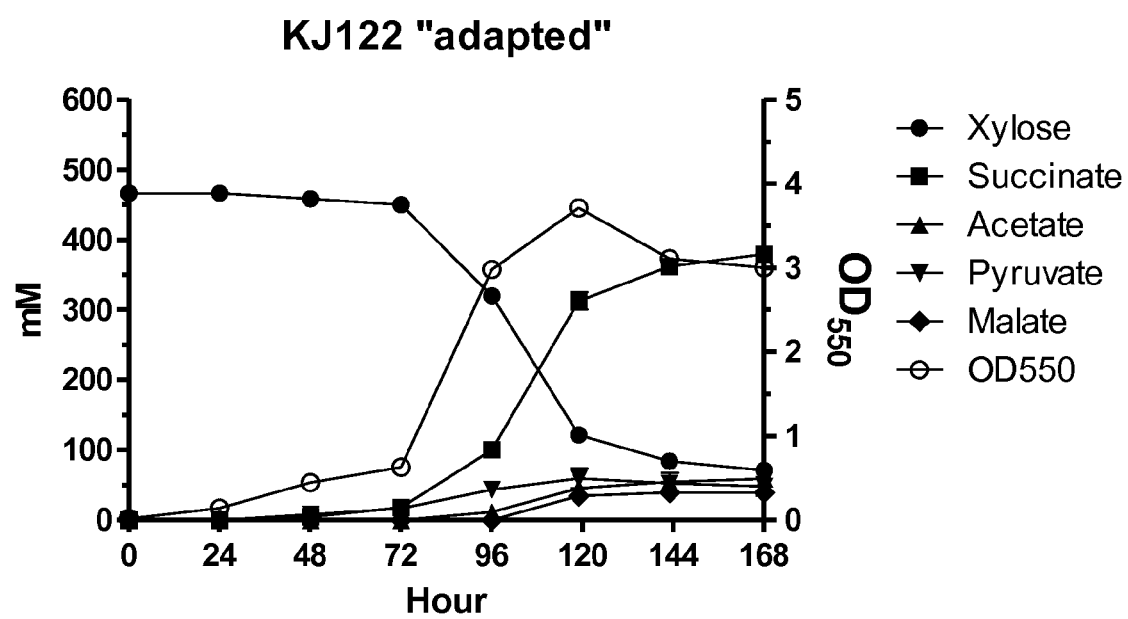
FIG. 2. Fermentation profile for KJ122 strain of *E. coli* adapted to metabolize xylose in mineral medium supplemented with 8% xylose. Fermentation was carried out for a total period of 168 hours. The xylose utilization shown in solid circles started around 72 hours accompanied by an increase in the bacterial cell density measured in terms of an increase in optical density at 550 nm shown in open circles. The increase in succinate concentration shown in solid squares occurred around 72 hours. Also shown in the figure are the changes in the concentration of acetate, pyruvate and malate in the medium during the course of 168 hours of fermentation.
Figure 3:
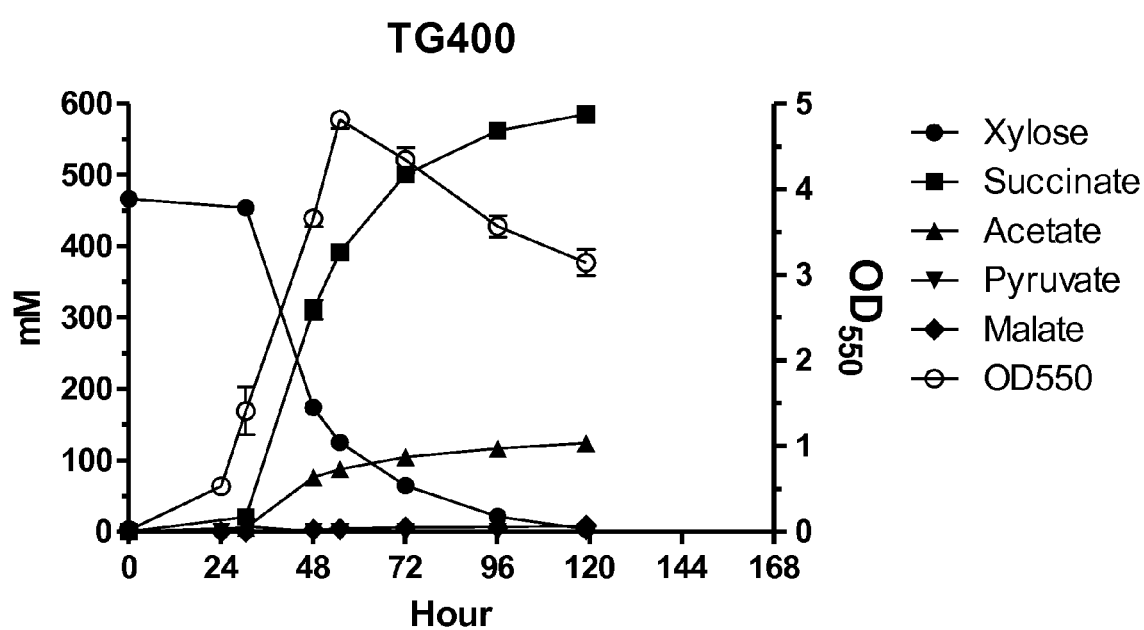
FIG. 3. Fermentation profile for TG400 strain of *E. coli* in mineral medium supplemented with 8% xylose. The fermentation profile was monitored for a period of 120 hours. The xylose utilization shown in solid circles started around 30 hours accompanied by an increase in the bacterial cell density measured in terms of an increase in optical density at 550 nm shown in open circles. The increase in succinate concentration shown in solid squares occurred around 30 hours. Also shown in the figure are the changes in the concentration of acetate, pyruvate, and malate in the medium during the course of 120 hours of fermentation.

As the results shown in FIGS. 1, 2, and 3 indicate, the xylose utilization as monitored by the disappearance of xylose in the growth medium showed a lag period of 96 hours both in the original KJ122 strain as well as in the "adapted "strain of KJ122. In the case of metabolically evolved TG400 strain, most of the xylose in the medium was consumed within the first 96 hours. In addition, for TG400, the succinic acid production did not show any lag period. Similarly, the cell growth for TG400 showed no lag period while the "adapted strain" of KJ122 and the original KJ122 stain showed an initial lag phase of about 72 hours (FIGS. 1 and 2). These observations clearly establish that the metabolically evolved TG400 strain has acquired a stable genotype for xylose utilization during metabolic evolution and this ability was not lost even when this strain was grown for several generations in the absence of xylose. On the other hand, the KJ122 strain adapted to grow in the medium containing only xylose, loses its ability to use xylose, when grown for several generations in the glucose containing medium in the absence of xylose. This "adapted strain" of KJ122 grown in the absence of xylose needed additional 96 hours to adapt itself again to use xylose as a source of carbon. Thus the "adapted strain" of KJ122 did not acquire any genetic modification during it adaption in the xylose containing medium for 96 hours.

TG400 while acquiring an ability to use xylose as a carbon source still retained its ability to use glucose as the source of carbon (Table 2).

Example 3

C5+C6 Co-Fermentation

Figure 4:
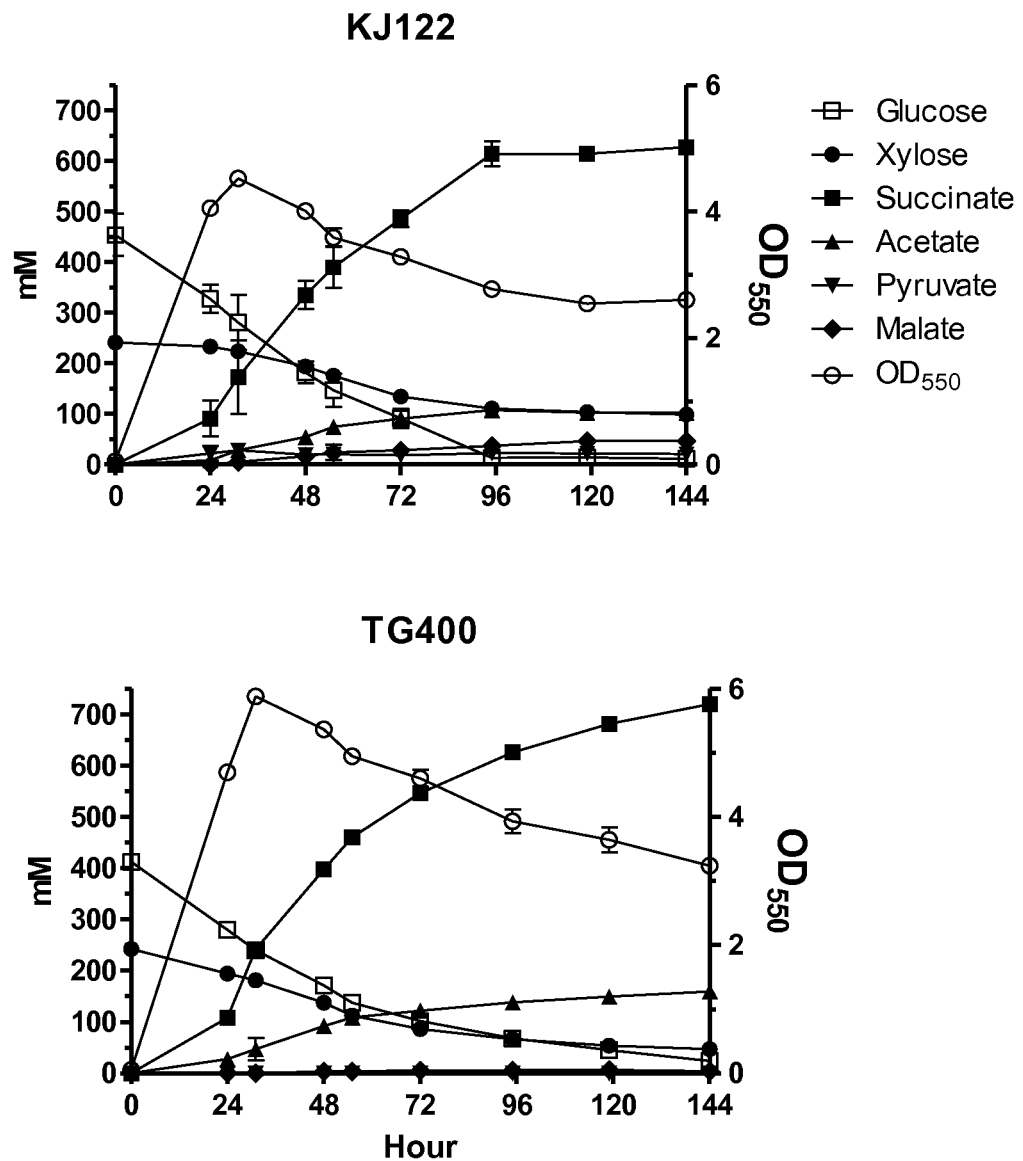
FIG. 4. Profile of mixed sugar fermentation by KJ122 and TG400 strains of *E. coli*. The fermentation was monitored for a total period of 144 hours. The fermentation medium contained both glucose and xylose. The glucose utilization as shown by a decrease in glucose concentration is shown by open squares. The xylose utilization as shown by a decrease in xylose concentration is shown by solid circles. The increase in the succinate concentration in the fermentation medium is shown by solid squares. The change in the cell density as measured by optical density at 550 nm during the course of 144 hours of fermentation is shown by open circles. Also shown in figures are the changes in the concentration of acetate, pyruvate and malate during the course of 144 hours of fermentation.

In KJ122 under anaerobic growth conditions, the C5 and C6 sugars are not simultaneously metabolized. The C6 sugars are generally metabolized first, and a lag is exhibited prior to C5 metabolism. Therefore it was essential to determine the fermentation characteristics of TG400 in the presence of equal amounts of both C6 and C5 sugars. As shown in FIG. 4, TG400 was able to use glucose and xylose at the same rate and produced succinic acid without any lag period. KJ122 was also able to use both xylose and glucose. However in the KJ122 strain, the xylose utilization started only after a substantial decrease in the glucose concentration. Further as shown in Table 3, TG400 used more xylose on a molar basis than glucose when compared to the xylose and glucose utilization by KJ122.

Example 4

Fermentation of Detoxified Bagasse Hydrolysate Enriched in C5 Sugars

Figure 5:
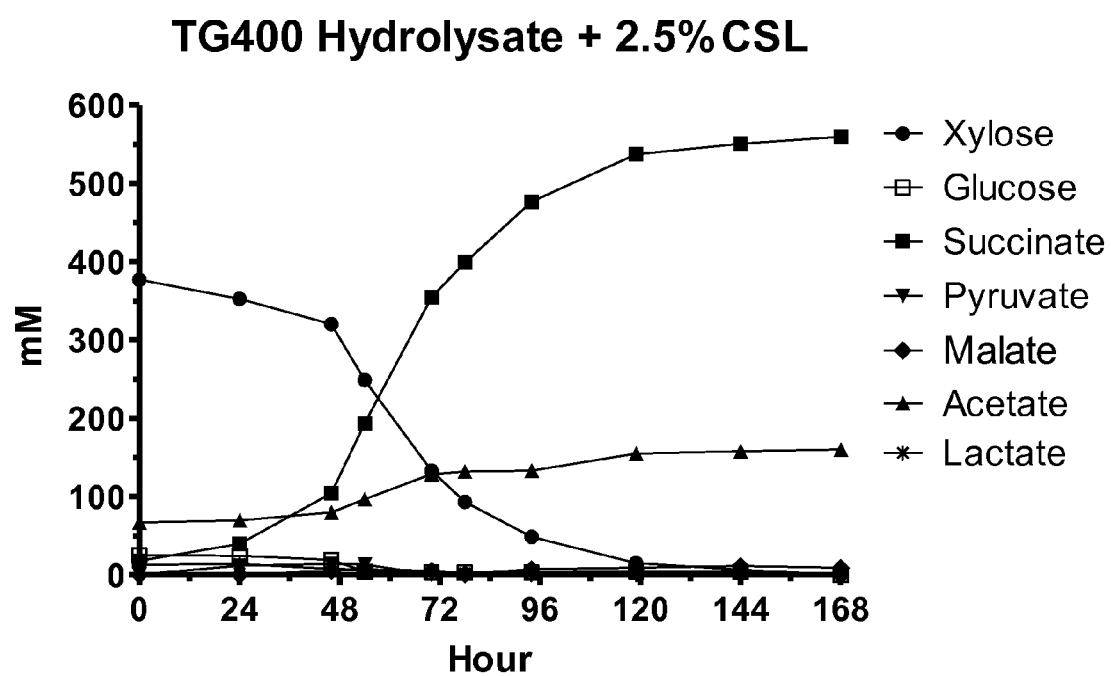
FIG. 5. Profile of fermentation of detoxified concentrated bagasse C5 hydrolysate supplemented with 2.5% (w/v) corn steep liquor by TG400 strain of *E. coli*. The fermentation was carried out for a period of 168 hours. The xylose utilization as measured by a decrease in the concentration of xylose is shown in solid circles. The increase in succinate concentration in the fermentation medium is shown by solid squares. Also shown in the figure are the changes in the concentration of pyruvate, acetate, malate and lactate in the medium during the course of 168 hours of fermentation.

TG400 strain obtained through metabolic evolution was tested for its ability to use xylose derived from a hydrolysis of bagasse. The concentrated bagasse hydrolysate was detoxified by means of treating it with 50 grams of charcoal for every kilogram of bagasse hydrolysate at 35° C. for 60 minutes in a rotary shaker at 200 rpm. The activated charcoal treated C5 enriched bagasse was pH adjusted, supplemented with AM1 mineral salts, betaine and trace elements and then filter sterilized. Hydrolysate comprised primarily of 8% (w/v) xylose (C5) and approximately 0.8% glucose (C6), 0.1% galactose (C6), 0.1% mannose (C6) and 0.002% arabinose (C5). The concentrated detoxified C5 sugars enriched bagasse hydrolysate was further supplemented with 2.5% w/v corn steep liquor and inoculated with TG400 strain to an initial $OD_{550}$ nm of 0.5. As the results shown in FIG. 5 indicate, within 120 hours, all the sugars in the culture medium were consumed and there was a steady production of succinate.

Example 5

Genomic Sequencing of KJ122 and TG400 Strains of Escherichia coli

The entire genome of the parent strain KJ122 and the TG400 strain derived from KJ122 through metabolic evolution were sequenced using an Illumina Genome Analyzer II at the Tufts University Core Facility in Boston Mass., USA. The Genome Analyzer II is provided by Illumina Sequencing Technology. The genomic data obtained for KJ122 and TG400 were compared to each other to identify the genetic changes accompanying the metabolic evolution of TG400 from KJ122. A comparative analysis of TG400 and KJ122 revealed a mutational change in the galP gene of TG400. The galP gene in TG400 showed a point mutation at the nucleotide position 889 of its open reading frame. The cytosine nucleotide at this position was changed to guanosine residue. As a result of this nucleotide change, the amino residue glycine was changed to aspartate. This mutation in the galP gene is referred as galP*. This mutation was the only difference between KJ122 and TG400 strains of bacteria at the nucleotide level.

Example 6

PCR and Sequence Analysis of galP Gene Sequences in TG400 and KJ122

Having established that there is a mutation in the galP gene sequence in the TG400 strain accounting for its ability to use xylose and glucose simultaneously, we used PCR techniques to obtain the galP gene from KJ122 and TG400. The PCR products obtained from TG400 as well as the PCR product from KJ122 were sequenced. As the sequence data revealed a point mutation that changes glycine residue at position 296 to an aspartate residue (Gly296 to Asp).

Example 7

Effect of galP Gene Deletion

Having established that there is a galP gene mutation in TG400 accompanying the ability to use glucose and xylose simultaneously, we decided to determine whether deletion of the entire galP gene would have the same phenotypic effect as seen in TG400 with a mutated galP gene. In these experiments we used KJ122 of E. coli as the parent strain.

Figure 6:
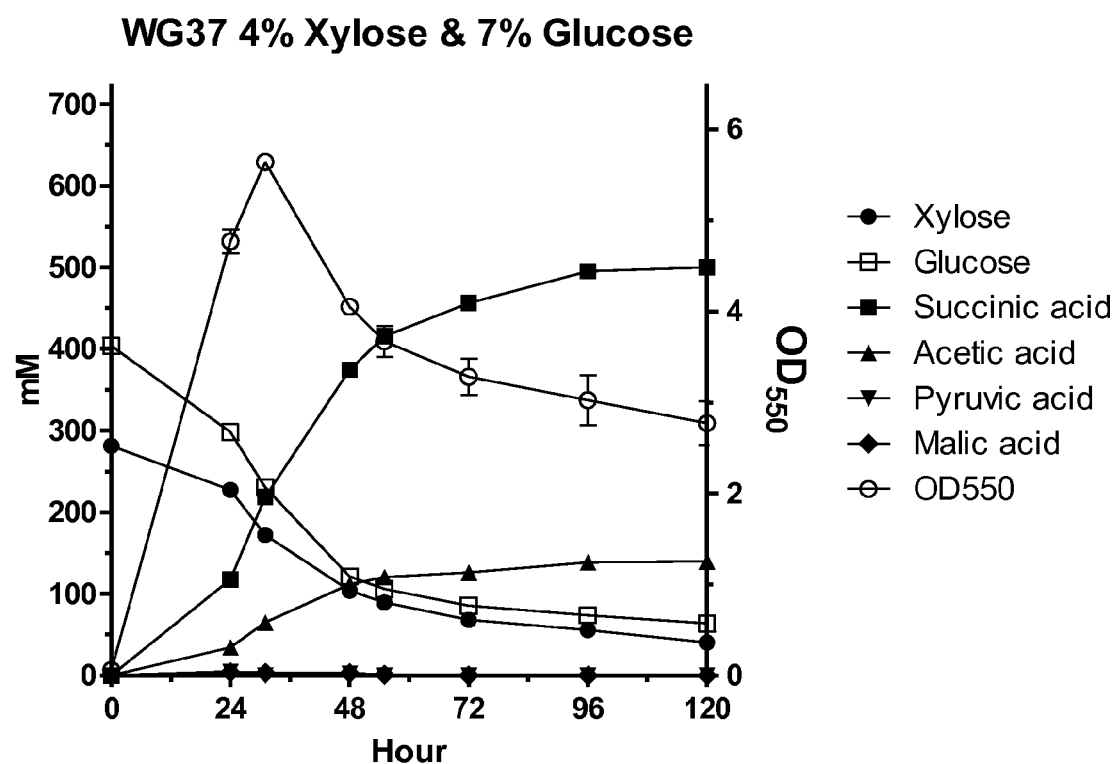
FIG. 6. Fermentation profile of WG37 strain of *E. coli* in a medium containing both glucose and xylose. Fermentation was carried out for a period of 120 hours. The glucose utilization as measured by a decrease in the glucose concentration in the medium is shown in open squares. The xylose utilization as measured by a decrease in the xylose concentration in the medium is shown in solid circles. The change in the bacterial cell density as measured by optical density at 550 nm during the course of 120 hours of fermentation is shown by open circles. The increase in the succinate concentration is shown in sold squares. Also shown in the figure are the changes in the concentration of acetic acid, pyruvic acid and malic acid during the course of 120 hours of fermentation.

We deleted the galP gene sequence from the KJ122 strain of E. coli to produce a new strain called WG37. We measured the growth kinetics, sugar utilization pattern and the succinic acid production in KJ122, TG400 and WG37 strains grown anaerobically in a minimal medium containing both glucose and xylose as the source of carbon. WG37 was able to use both glucose and xylose simultaneously during the course of 96 hours (FIG. 6). Its growth kinetics as well as the sugar utilization patterns were similar to that of TG400 which has a mutated form of galP gene. In KJ122, the glucose was completely consumed within 72 hours while the xylose utilization showed an initial lag of 24 hours. Both in TG400 and in WG37, the glucose was not exhausted even after 96 hours of growth and a significant amount of glucose remained in the medium at 96 hours of growth. In addition, both in TG400 and WG37, the xylose utilization could be detected as early as 12 hours.

Figure 7:
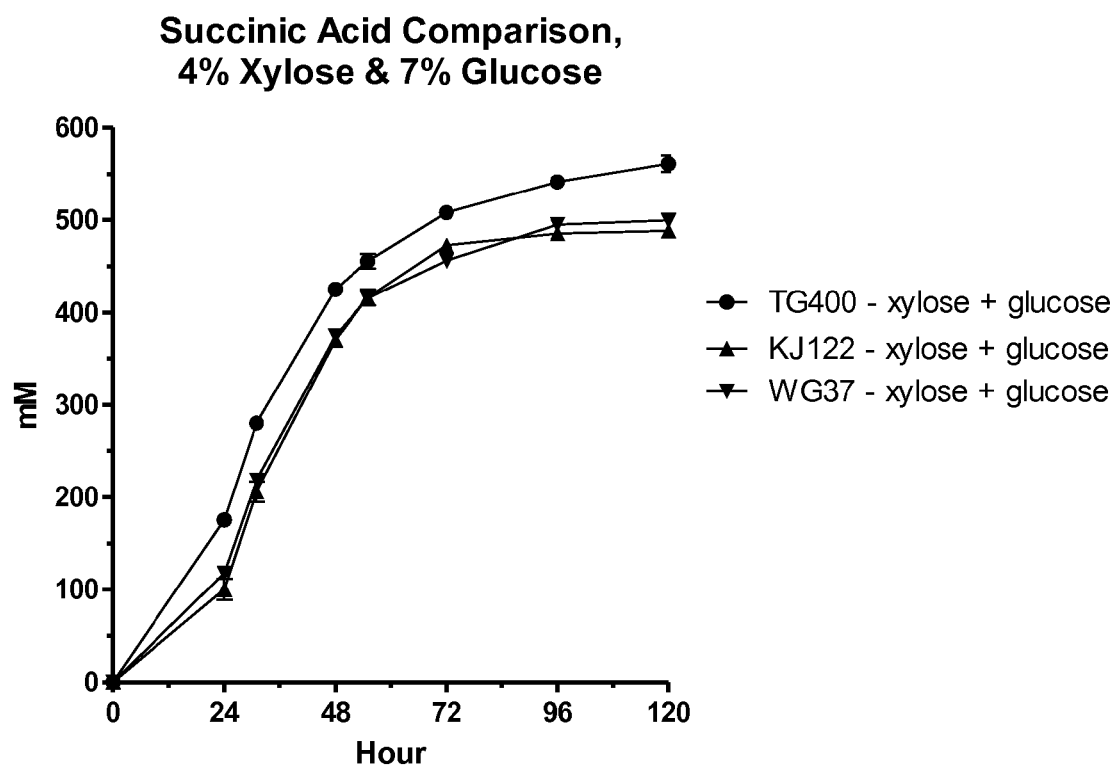
FIG. 7. Side-by-side comparison of succinic acid production by TG400, WG37 and KJ122 strains of bacteria in the growth medium containing 4% xylose and 7% glucose. The fermentation was carried out for a period of 120 hours. The increase in the concentration of succinic acid in the fermentation medium with TG400 (solid circles), KJ122 (solid triangle), and WG37 (inverted triangle) strains of *E. coli* was monitored for a period of 120 hours.
Figure 8:
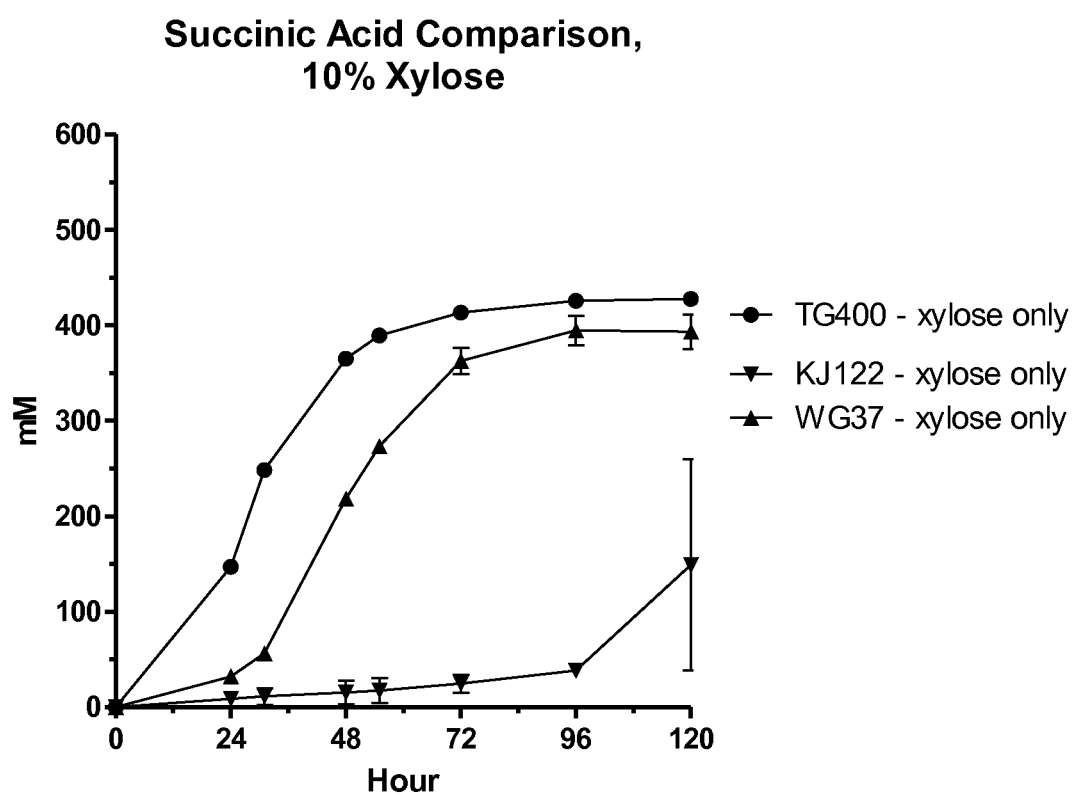
FIG. 8. Side-by-side comparison of succinic acid production by TG400, WG37 and KJ122 strains of bacteria in the growth medium containing only 10% xylose. The fermentation was carried out for a period of 120 hours. The increase in the concentration of succinic acid in the fermentation medium with TG400 (solid circles), KJ122 (inverted triangle), and WG37 (triangle) strains of *E. coli* was monitored for a period of 120 hours.
Figure 9:
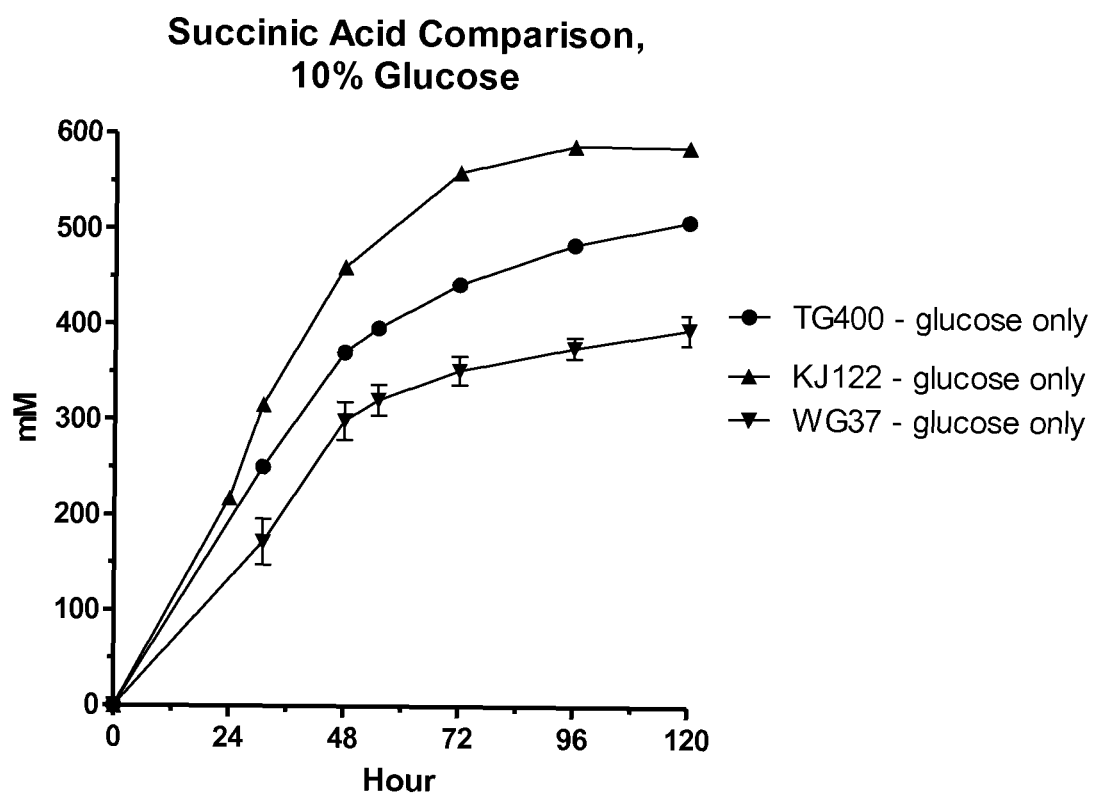
FIG. 9. Side-by-side comparison of succinic acid production by TG400, WG37 and KJ122 strains of bacteria in the growth medium containing only 10% glucose. The fermentation was carried out for a period of 120 hours. The increase in the concentration of succinic acid in the fermentation medium with TG400 (solid circles), KJ122 (triangle), and WG37 (inverted triangle) strains of *E. coli* was monitored for a period of 120 hours.

FIGS. 7, 8 and 9 show the side-by-side comparison of kinetics of succinic acid production in all the three strains used in the present invention. When grown in the medium containing 4% xylose and 7% glucose, all the strains showed a similar kinetics for succinic acid production irrespective of whether they had an intact galP gene sequence or not. In the medium containing the mixed sugars, TG400 showed a slightly higher rate for succinic acid production (FIG. 7).

In the medium containing xylose as the only source of carbon, the TG400 and WG37 strains showed much faster rates for succinic acid production when compared to the rate of succinic acid production by KJ122 strain (FIG. 8).

In the medium containing glucose as the only source of carbon, the two bacterial strains TG400 and WG37 with deletions in galP gene sequence showed slower rates for succinic acid production when compared to the rate of succinic acid production by KJ122. (FIG. 9).

Example 8

Effect of G297D Point Mutation in galP on Xylose Utilization

In order to examine the effect of point mutation that results in G297D (replacement of glycine residue at position 297 with aspartate residue in the GalP protein) on the growth and succinate production in the fermentation medium containing xylose as the sole source of carbon, the G297D mutation was introduced into the galP gene sequence in the KJ122 strain. SI014 (KJ122 ΔgalP::galP*) was created by PCR amplifying the mutant galP* gene from TG400 using the primers 17ASP-galP (SEQ ID No. 9) and 18SPgalP (SEQ ID NO. 10) and then recombining within WG35 (KJ122 ΔgalP::kan-sacB) which was expressing lambda red recombinase from a temperature conditional plasmid, pKD46. Plasmids pKD46 was then removed by growth at an elevated temperature (Datsenko and Waner, 2000).

KJ122 was obtained off a MacConkey lactose plate. SI014 (KJ122galP*) was taken from an LB 2% glucose plate. Scrapes from the plates were used to inoculate 25 mls LB 2% glucose. Cultures were grown for 8 hours at 37° C., 150 rpm. Final $OD_{600}$ for these cultures was 0.71 for KJ122 and 0.58 for SI014. 5 mls of each LB glucose culture was used to inoculate a 300 ml seed fermentor containing AM1 10% glucose medium. These fermentations were held at pH 7.0, 37° C. for 24 hours. Final $OD_{600}$ for these cultures was 3.82 for KJ122 and 2.89 for SI014. These cultures were used to inoculate triplicate fermentors containing AM1 10% xylose medium. Target final $OD_{600}$ is 0.1, so for KJ122, 7.85 mls was used and for SI014, 10.38 mls was used to inoculate a 300 ml fermentation. Fermentations were maintained at pH 7.0 and 37 C for 97 hours. Samples were taken daily for $OD_{600}$ and metabolite analysis. All metabolite and growth data was graphed and analyzed (2 way ANOVA) using GraphPad Prism.

Figure 10:
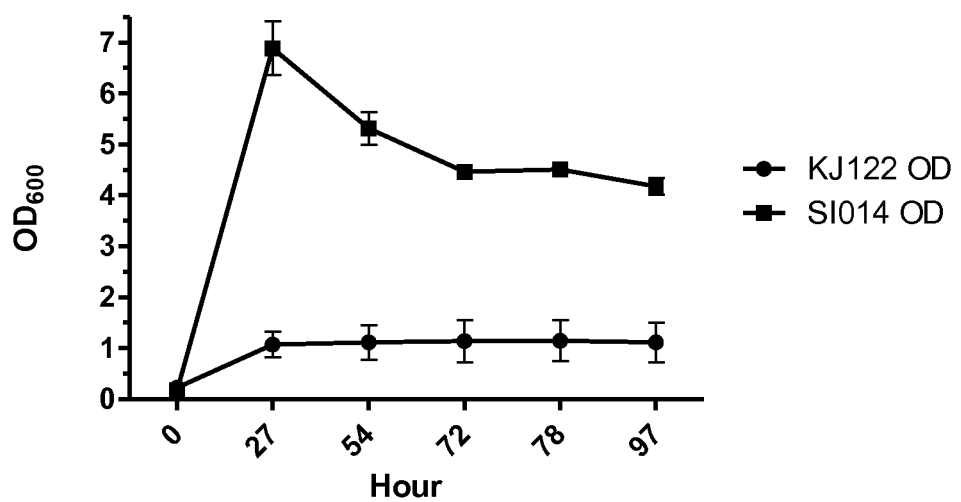
FIG. 10. Growth Profile KJ122 and SI014 strains of *E. coli* in a growth medium containing xylose as the sole source of carbon. The bacterial growth was monitored in terms of optical density at 600 nm for a total period 97 hours. KJ122 strain of (solid circles) showed only a very slow growth. On the other hand, SI014 strain (solid squares) showed a fast growth within 27 hours followed by a slow decrease in the cell density.
Figure 11:
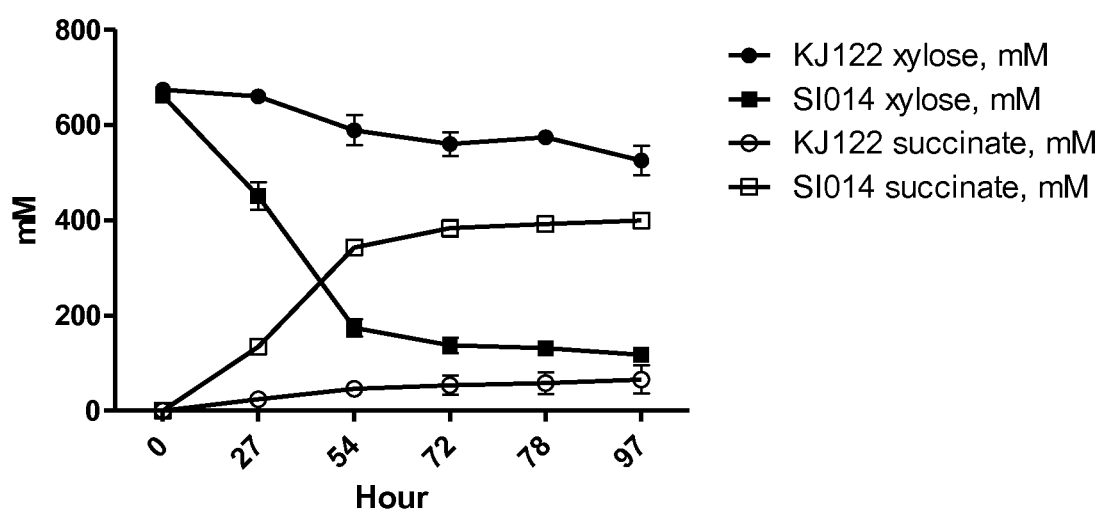
FIG. 11. Profile for xylose utilization and succinate production by KJ122 and SI014 strains of *E. coli* in a medium containing xylose as the sole source of carbon. The xylose utilization was measured in terms of a decrease in the xylose concentration in the medium for a period of 97 hours, Xylose utilization with SI014 strain (solid squares) was much faster when compared to the xylose utilization by KJ122 strain (solid circle). Similarly, the succinic production with SI014 strain (open squares) was much faster when compared to the succinic acid production by KJ122 strain (open circles).

The growth profile for E. coli strain SI014 which contains a point mutation in the galP gene that results in 1 amino acid change at position 297, is shown in FIG. 10. It is very clear by $OD_{600}$ values that, on a medium containing xylose as the sole source of carbon, SI014 strain grows more quickly and more densely than KJ122. The only known difference between these two strains is the point mutation in the galP gene. FIG. 11 shows the increased consumption of xylose and the concomitant increase in succinic acid production for strain SI014 compared to KJ122.

The applicants' invention has been described in detail above with particular reference to preferred embodiment. A skilled practitioner familiar with the above detailed description can make any modification without departing from the spirit of the claims that follow.

TABLE 1

Nucleotide sequence of the primers used in the present invention

| Primer No. | Primer Name | Primer sequence |
|---|---|---|
| SEQ ID No. 1 | BY38 | 5' cagcgtttaatctatgatgatataactcaattattttca 3' |
| SEQ ID No. 2 | BY39 | 5' ggcgatagggagacgggatgttttc 3' |
| SEQ ID No. 3 | 49a | 5' ccgattacaccaaccacaac 3' |
| SEQ ID No. 4 | 49b | 5' ggcgaatttcatagctttcc 3' |
| SEQ ID No. 5 | 50a | 5' gaaataggcgctcacgatta 3' |
| SEQ ID No. 6 | 50b | 5' aaacgtcattgccttgtttg 3' |
| SEQ ID No. 7 | 51a | 5' taaccatattggagggcatcatgcctgacgctaaaaaacagggcggtcaaacaag gcaactagcgcatgcatccattta 3' |
| SEQ ID No. 8 | 51b | 5' ctgcaagaggtggcttcctccgcgatgggaggaagcttggggagattaatcgtgag cgcctggcgaagaactccagcatga 3' |
| SEQ ID No. 9 | 17ASPga1P | 5' acccagcacgttttccatca 3' |
| SEQ ID No. 10 | 18SPga1P | 5' tgcgttcaaaggccagcctc 3' |

TABLE 2

Glucose fermentation by KJ122 and TG 400 strains of E. coli.

| | KJ122 | | TG400 | |
|---|---|---|---|---|
| | mM* | g/L* | mM* | g/L* |
| Glucose consumed | 573 | 103 | 368 | 66 |
| Succinic acid | 742 | 88 | 492 | 58 |
| Yield | 1.29 (mol/mol) | | 1.35 (mol/mol) | |
| Yield (%) (Theoretical) | 75% | | 78% | |

*All the values provided here are normalized for base addition.

TABLE 3

Co-fermentation of C5 and C6 sugars by KJ122 and TG400 stains of E. coli. TG400 and KJ122 were on glucose containing medium prior to experiment. TG400*** was actively growing on xylose prior to experiment. The results are average of two fermentations.

| | TG400 | | KJ122 | | TG400*** | |
|---|---|---|---|---|---|---|
| | mM* | g/L* | mM* | g/L* | mM* | g/L* |
| Xylose consumed | 195 | 29 | 142 | 221 | 221 | 33 |
| Glucose consumed | 389 | 70 | 448 | 80.8 | 366 | 66 |
| Succinic acid | 721 | 85 | 633 | 75 | 810 | 96 |
| Theoretical yield | 945 | 112 | 971 | 115 | 948 | 112 |
| Yield (%) | 76% | | 65% | | 86% | |

*All the values provided here are normalized for base addition

TABLE 4

Yields from batch fermentations (8% xylose) - KJ122 vs. TG400

| Strain | Conditions | Succinate (g/L) | Acetate (g/L) | Malate (g/L) | Pyruvate (g/L) | Yield[b] (%) | Time (hrs) |
|---|---|---|---|---|---|---|---|
| KJ122[c] | [a, c] | 54 | 4 | 5 | 8 | 61 | 192 |
| KJ122 | [a] | 50 | 4 | 1 | 7 | 61 | 120 |
| TG400 | [a] | 70 | 7. | 0 | 0 | 76 | 96 |
| KJ122 | C5 + C6[d] | 75 | 7 | 5 | 2 | 65 | 120 |
| TG400 | C5 + C6[d] | 96 | 10 | 1 | 0 | 86 | 120 |
| TG400 | Hydrolysate[e] | 66 | 6 | 1 | 0 | 92 | 120 |

[a] Batch fermentations were performed in triplicate in AM1 mineral salts media supplemented with 0.03M $KHCO_2$, 1 mM betaine and 8% xylose, unless otherwise noted; pH was controlled at 7.0 by automatic addition of 1.2N KOH and 2.4M $K_2CO_3$. Titers are normalized for base addition.
[b] Yields are based on metabolized sugar assuming a maximum theoretical yield of 1.12 g of succinic acid per g of xylose.
[c] First xylose fermentation (in duplicate)
[d] Initial sugar concentration: 4% xylose, 7% glucose, 0.4% galactose, 0.3% mannose, 0.5% arabinose
[e] Concentrated detoxified C5 hydrolysate from bagasse (see FIG. 5 legend). Initial sugar concentration was: 56.6 g/L xylose, 4.5 g/L glucose, 0.0009 g/L galactose, 2.7 g/L arabinose. All sugars were consumed. Initial acetic acid from pretreatment process 4.04 g/L) was subtracted from final acetate to determine acetic acid produced during fermentation.

REFERENCES

All references are listed for the convenience of the reader. Each reference is incorporated by reference in its entirety.

U.S. Pat. No. 5,168,056
U.S. Pat. No. 5,169,768
U.S. Pat. No. 5,602,030
U.S. Pat. No. 6,962,794
U.S. Pat. No. 7,223,567
U.S. Pat. No. 7,371,558
U.S. Pat. No. 7,524,660
U.S. Pat. No. 7,629,162
U.S. Patent Application Publication No. 2004/0214294
U.S. Patent Application Publication No. 2007/0037265
U.S. Patent Application Publication No. 2008/0176302
U.S. Patent Application Publication No. 2009/0148914
International Patent Application Publication No. WO 2008/115958
International Patent Application Publication No. WO 2010/115067

Bertilsson, M., Olofsson, K., Liden, G. (2009) "Prefermentation improves xylose utilization in simultaneous saccharification and co-fermentation of pretreated spruce." *Biotechnol Biofuels* 2: 8 (Biomed Central. Published Apr. 8, 2009)

Biville, F., Turlin, E., Gasser, F. (1991) "Mutants of *Escherichia coli* producing pyrroloquinoline quinine." *J Gen Microbio* 137: 1775-1782.

Cairns, M. T., McDonald, T. P., Horne, P., Henderson, P. J. (1991) "Cytochalasin B as a probe of protein structure and substrate recognition by the Galactose/H+ transporter of *Escherichia coli*." *J Biol Chem* 266:8176-8183.

Chen, R., Yap, W. M. G. J., Postma, P. W., Bailey, J. E. (2000) "Comparative studies of *Escherichia coli* strains using different glucose uptake systems: Metabolism and energetic." *Biotechnol Bioeng* 56: 583-590.

Chen, T., Zhang, J., Liang, L., Yang, R., Lin, Z. (2009) "An in vivo, label-free quick assay for xylose transport in *Escherichia coli*." *Anal Biochem* 390: 63-67.

Chin, J. W., Khankal, R., Monroe, C. A., Maranas, C. D., Cirino, P. C. (2009) "Analysis of NADPH supply during xylitol production by engineered *Escherichia coli*." *Biotechnol Bioeng* 102: 209-220.

Cirino, J. W., Chin, J. W., Ingram, L. O. (2006) "Engineering *Escherichia coli* for xylitol production from glucose-xylose mixtures." *Biotechnol Bioeng* 95: 1167-1176.

Castro, R., Neves, A. R., Fonseca, L. L. Pool, W. A., Kok, J., Kuipers, O. P., Santos, H. (2009) "Characterization of the individual glucose uptake systems of *Lactococcus lactis*: mannose-PTS, cellobiose-PTS and the novel GlcU permease." *Mol Microbio* 71: 795-806.

Causey, T. B., Shamugam, K. T., Yomano, L. P., Ingram, L. O. (2004) "Engineering *Escherichia coli* for efficient conversion of glucose to pyruvate." *Proc Natl Acad Sci USA* 101:2235-2240.

De Anda, R., Lara, A. R., Hernandez, V., Hernandez-Montavlo, V., Gosset, G., Bolivar, F., Ramirez, O. T. (2006) "Replacement of the glucose phosphotransferase transport system by galactose permease reduces acetate accumulation and improves process performance of *Escherichia coli* for recombinant protein production without impairment of growth rate." *Metab Eng* 8: 281-290.

Deutscher, J., Francke, C., Postma, P. W. (2006) "How phosphotransferase system-related protein phosphorylation regulates carbohydrate metabolism in bacteria." *Microbiol Mol Bio Rev* 70:939-1031.

Deutscher, J. (2008) "The mechanism of carbon catabolite repression in bacteria." *Curr Opin Microbiol* 11:87-93.

Dien, B. S., Nichols, N. N., Bothast, R. J. (2002) "Fermentation of sugar mixtures using *Escherichia coli* catabolite repression mutants engineered for production of L-lactic acid." *J Ind Microbiol Biotechnol* 29: 221-227.

Flores, N., Leal, L., Sigala, J. C., deAnda, R., Escalante, A., Martinez, A., Ramirez, O. T., Gosset, G., Boliar, F. (2007) "Growth recovery on glucose under aerobic condition of an *Escherichia coli* strain carrying a phosphoenolpyruvate: carbohydrate phosphotransferase system deletion by inactivating arcA and overexpressing the genes coding for glucokinase and galactose permease." *J Mol Microbiol Biotechnol* 13: 105-116.

Gorke, B., Stulke, J. (2008) "Carbon catabolite repression in bacteria; many ways to make the most out of nutrients." *Nat Rev Microbiol* 6: 613-624.

Henderson, P. J. F., Giddens, R. A., Jones-Mortimer, C. J. (1977) "Transport of galactose, glucose and their molecular analogues by *Escherichia coli* K12." *Biochem J* 162: 309-320.

Henderson, P. J. (1990) "Proton-linked sugar transport systems in bacteria." *J Bioenergy Biomem* 22: 525-569.

Hernandez-Montalvo, V., Valle, F., Bolivar, F., Gosset, G. (2001) "Characterization of sugar mixtures utilization by an *Escherichia coli* mutant devoid of the phosphotransferase system." *App. Microbiol Biotechnol* 57: 186-191.

Ho, N. W. Y., Chen, Z., Brainard, A. P. (1998) "Genetically engineered *Sacchromyces* yeast capable of effective cofermentation of glucose and xylose." *App Environ Microbiol* 64: 1852-1859.

Jantama, K., Haupt, M. J., Svoronos, S. A., Zhang, X., Moore, J. C., Shanmugham, K. T., Ingram, L. O. (2008a) "Combining metabolic engineering and metabolic evolutions to develop nonrecombinant strains of *Escherichia coli* C that produce succinate and malate." *Biotechnol Bioeng* 99: 1140-1153.

Jantama, K., Zhang, X., Moore, J. C., Shanmugam, K. T., Svoronos, S. A., Ingram, L. O. (2008b) "Eliminating side products and increasing succinate yields in engineered strains of *Escherichia coli* C." *Biotechnol Bioeng* 101: 881-893.

Kasahara, T., Kasahara, M. (2003) "Transmembrane segments 1, 5, 7, and 8 are required for high-affinity glucose transport by *Saccharomyces cerevisiae* Hxt2 tranporter." *Biochem J* 372: 247-252.

Kasahara, T., Ishigure, M., Kasahara, M. (2004) "Comprehensive chimeric analysis of amino acid residues critical for high affinity glucose transport by Hxt2 of *Saccharomyces cerevisiae*." *J Biol Chem* 279: 30274-30278.

Kasahara, T., Maeda, M., Ishiguro, M., Kasahara, M. (2007) "Identification by comprehensive chimeric analysis of a key residue responsible for high affinity glucose transport by yeast HXT2." *J Biol Chem* 282:13146-13150.

Kasahara, T., Ishiguro, M., Kasahara, M. (2006) "Eight amino acid residues in transmembrane segments of yeast glucose transporter HXt2 are required for high affinity transport." *J Biol Chem* 281: 18532-18538.

Khankal, R., Chin, J. W., Cirino, P. C. (2008) "Role of xylose transporters in xylitol production from engineered *Escherichia coli*." *J Biotechnol* 134: 246-252.

Kilian, S. G., Uden van, N. (1988) "Transport of xylose and glucose in the xylose fermenting yeast *Pichia stipitis*." *App Microbiol Biotechnol* 27: 545-548.

Kim, Y., Ingram, L. O., Shanmugam, K. T. (2007) "Construction of an *Escherichia coli* K-12 mutant for homoethnologenic fermentation of glucose or xylose without foreign genes." *Appl Environ Microbiol* 73: 1766-1771.

Kuyper, M., Toirkens, M. J., Diderich, J. A., Winkler, A. A., Dijke van, J. P., Pronk, J. T. (2005) "Evolutionary engineering of mixed-sugar utilization by a xylose-fermenting *Saccharomyces cerevisiae* strain." *FEMS Yeast Res* 5:925-934.

Law, C. J., Maloney, P. C., Wang, D. N. (2008) "Ins and outs of major facilitator superfamily antiporters." *Annu Rev Microbiol* 62:289-305.

Leandro, M. J., Goncalves, P., Spencer-Martins, I. (2006) "Two glucose/xylose transporter genes from the yeast *Candida intermedia*: first molecule characterization of a yeast xylose-H+ symporter." *Biochem J*. 395: 543-549.

Leandro, M. J., Spencer-Martins, I., Goncalves, P. (2008) "The expression in *Saccharomyces cerevisiae* of a glucose/xylose symporter from *Candida intermedia* is affected by the presence of a glucose/xylose facilitator." *Microbiol* 154: 1646-1655.

Leandro, M. J., Fonseca, C., Goncalves, P. (2009) "Hexose and pentose transport in ascomycetous yeasts: an overview." *FEMS Yeast Res* 9:511-525.

Lengeler, J. W., Jahreis, K. (2009) "Bacterial PEP-dependent carbohydrate: phosphotransferase systems couple sensing and global control mechanisms." *Contrib Microbiol* 16: 65-87.

Lindsay, S. E., Bothast, R. J., Ingram, L. O. (1995) "Improved strains of recombinant *Escherichia coli* for ethanol production from sugar mixtures." *Appl Micorbiol Biotechnol* 43: 70-75.

Macpherson, A. J. S., Jones-Mortimer, M. C., Horne, P., Henderson, P. J. F. (1983) "Identification of the GalP galactose Transport protein of *Escherichia coli*." *J Biol Chem* 258: 4390-4396.

Marsh, D., Henderson, P. J. F. (2001) "Specific spin labeling of the sugar-H$^+$ symporter, GalP, in cell membranes of *Escherichia coli*; site mobility and overall rotational diffusion of the protein." *Biochim Biophys Acta* 1510: 464-473.

Martin, G. E. M., Seamont, K. B., Brown, F. M., Shanahan, M. F., Roberts, P. E. Henderson, P. J. F. (1994) "Forskolin specifically inhibits the bacterial galactose-H+ transport protein, GalP." *J Biol Chem* 269: 24870-24877.

Martinez, A., Grabar, T. B., Shanmugam, K. T., Yomano, L. P. York, S. W., Ingram, L. O. (2007) "Low Salt medium for lactate and ethanol production by recombinant *Escherichia coli* B." *Biotechnol Lett* 29: 397-404.

McDonald, T. P., Walmsley, A. R., Henderson, P. J. F. (1997) "Asparagine 394 in putative helix 11 of the galactose-H+ symport protein (GalP) from *Escherichia coli* is associated with the internal binding site for cytochalasin B and sugar." *J Biol Chem* 272:15189-15199.

McDonald, T. P., Henderson, P. J. F. (2001) "Cysteine residues in the D-galactose-H+ symport protein of *Escherichai coli*: effects of mutagenesis on transport, reaction with N-ethylmaleimide and antibiotic binding." *Biochem J* 353: 709-717.

Nichols, N. N., Dien, B. S., Bothast, R. J. (2001) "Use of catabolite repression mutants for fermentation of sugar mixtures to ethanol." *Appl Microbiol Biotechnol* 56: 120-125.

Pao, S. S., Paulsen, I. T., Saier Jr, M. H. (1998) "Major facilitator suprefamily." *Microbiol Mol Bio Rev* 62: 1-34.

Patching, S. G., Henderson, P. J., Herbert, R. B., Middleton, D. A. (2008) "Solid-state NMR spectroscopy detects interactions between tryptophan residues of the *E. coli* sugar transporter GalP and the alpha-anomer of the D-glucose substrate." *J Am Chem Soc* 130: 1236-1244.

Patching, S. G., Psakis, G., Baldwin, S. S., Baldwin, J., Henderson, P. J., Middleton, D. A. (2008) "Relative substrate affinities of wild-type and mutant forms of the *Escherichia coli* sugar transporter GalP determined by solid-state NMR." *Mol Membr Biol* 25: 474-484.

Qaidl, S. E., Allemand, F., Oberto, J., Plumbridge, J. (2009) "Repression of galP, the galactose transporter in *Escherichia coli*, requires the specific regulator of N-acetylglucosamine metabolism." *Mol Microbiol* 71: 146-157.

Runquist, D., Fonseca, C., Radstrom, P., Spencer-Martins, I., Hahn-Hagerdal, B. (2009) "Expression of the Gxf1 transporter from *Candida intermdia* improves fermentation performance in recombinant xylose-utilizing *Saccharomyces cerevisiae*." *Appl Microbiol Biotechnol* 82: 123-130.

Saier, M. H. Jr., Bromberg, F. G., Roseman, S. (1973) "Characterization of constitutive galactose permease mutants in *Salmonella typhimurium*." *J Bacteriol* 113:512-514.

Saloheimo, A., Rauta, J., Stasyk, O. V., Sibirny, A. A., Penttila, M., Ruohonen, L. (2007) "Xylose transport studies with xylose-utilizing *Saccharomyces cervisiae* strains expressing heterologous and homologous permeases." *Appl Microbiol Biotechnol* 74: 1041-1052.

Sanchez, A. M., Bennett, G. N., San, K. Y. (2005) "Efficient succinate production from glucose through over expression of pyruvate carboxylase in an *Escherichia coli* alcohol dehydrogenase and lactate dehydrogenase mutant." *Biotechnol Prog* 21: 358-365.

Sasaki, M., Jojima, T., Inui, M., Yukawa, H. (2008) "Simultaneous utilization of D-cellobiose, D-glucose, and D-xylose by recombinant *Corynebacterium glutamicum* under oxygen-deprived conditions." *Appl Microbiol Biotechnol* 81: 691-699.

Sedlak, M., Ho, N. W. (2004) "Characterization of the effectiveness of hexose transporters for transporting xylose during glucose and xylose co-fermentation by a recombinant *Saccharomyces* yeast." *Yeast* 21: 671-684.

Soberon, X., Saier Jr, M. H. (2006) "Engineering transport protein function: theoretical and technical consideratios using the sugar-transporting phosphotransferase system of *Escherichia coli* as a model system." *J Mol Microbiol Biotechnol* 11: 302-307.

Trinh, C. T., Unrean, P., Sriene, F. (2008) "Minimal *Escherichia coli* cell for the most efficient production of ethanol from hexoses and pentoses." *App Environ Microbiol* 74: 3634-3643.

Venter, H., Ashcroft, A. E., Keen, J. N., Henderson, P. J. F., Herbert, R. B. (2002) "Molecular dissection of membrane-transport proteins: mass spectrometry and sequence determination of the galactose-H+ symport protein, GalP of *Escherichai coli* and quantitative assay of the incorporation of [ring-2-$^{13}$C]histidine and $^{15}$NH$_3$." *Biochem J* 363: 243-252.

Wahlbom, C. F., Otero, R. C., Zyl van, W. H., Hahn-Hagerdal, B., Jonsson, L. J. (2003) "Molecular analysis of a *Saccharomyces cerevisae* mutant with improved ability to utilize xylose shows enhanced expression of proteins involved in transport, initial xylose metabolism, and the pentose phosphate pathway." *App Environ Microbiol* 69:740-746.

Wang, Q., Wu, C., Chen, T., Chen, X., Zhao, X. (2006) "Expression of galactose permease and pyruvate carboxylase in *Escherichia coli* ptsG mutant increases the growth rate and succinate yiled under anaerobic conditions." *Biotechnol Lett* 28: 89-93.

Yi, J., Drathas, K. M., Frost, J. W. (2003) "Altered glucose transport and shikimate pathway product yields in *E. coli*." *Biotechnol Prog* 19: 1450-1459.

Zhang, X., Jantama, K., Moore, J. C., Jarboe, L. R., Shanmugam, K. T., Ingram, L. O. (2009) "Metabolic evolution of energy-conserving pathways for succinate production in *Escherichia coli*." *Proc Natl Acad Sci USA* 106: 20180-20185.

We claim:

1. An isolated *Escherichia coli* bacterial cell comprising a mutation in galactose symporter (galP) gene, wherein said bacterial cell comprises at least one mutation that decreases the activity of PEP-dependent phosphotransferase system and utilizes C5 and C6 sugars simultaneously to produce an industrially useful chemical and said mutation in GalP gene comprises replacement of a glycine residue at position 297 with aspartic acid residue.

2. The isolated *Escherichia coli* bacterial cell of claim 1, further comprising at least one mutation that increases the activity of at least one non-PTS sugar transporter.

3. The isolated *Escherichia coli* bacterial cell of claim 2, wherein said non-PTS sugar transporter is an ATP binding cassette transporter.

4. The isolated *Escherichia coli* bacterial cell of claim 2, wherein said non-PTS sugar transporter is a member of major facilitator super family.

5. The isolated *Escherichia coli* bacterial cell of claim 1, further comprising at least one mutation that inactivates the expression of one or more genes involved in a fermentation pathway.

6. The isolated *Escherichia coli* bacterial cell of claim 1, further comprising at least one mutation that inactivates one or more genes associated with the tricarboxylic acid cycle.

7. The isolated *Escherichia coli* bacterial cell of claim 1, further comprising mutation in at least one of the genes selected from a group consisting of gene coding for phosphoenolpyruvate carboxylase, gene coding for NADH dependent malic enzyme, and gene coding for NADPH dependent malic enzyme.

8. The isolated *Escherichia coli* bacterial strain of claim 1, further comprising an exogenous pyruvate carboxylase.

9. The isolated *Escherichia coli* bacterial strain of claim 8, wherein said pyruvate carboxylase is from *Lactobacillus lactis* or *Sorghum vulgare* or *Rhizobium etli*.

10. The isolated *Escherichia coli* bacterial cell of claim 1, further comprising increased phosphoenol pyruvate carboxykinase activity.

11. The isolated *Escherichia coli* bacterial cell of claim 10, wherein increased levels of phosphoenol pyruvate carboxykinase activity result from a mutation in pck gene.

12. The isolated *Escherichia coli* bacterial cell of claim 11, wherein said mutation is in the promoter region of said pck gene.

13. A process for the microbial production of an organic dicarboxylic acid comprising:

a. providing an isolated *Escherichia coli* bacterial cell having a mutation in galactose symporter (galP) gene comprises at least one mutation that decreases the activity of PEP-dependent phosphotransferase system and utilizes C5 and C6 sugars simultaneously to produce an industrially useful chemical dicarboxylic acid and said mutation in GalP gene comprises replacement of a glycine residue at position 297 with aspartic acid residue;
b. culturing the bacterial cell of step (a) in a medium containing both pentose and hexose sugars simultaneously; and
c. optionally recovering the organic dicarboxylic acid from the culture medium.

* * * * *